United States Patent
Sharma et al.

(10) Patent No.: US 9,931,394 B2
(45) Date of Patent: Apr. 3, 2018

(54) SOLUBLE HIV-1 ENVELOPE GLYCOPROTEIN TRIMERS

(71) Applicants: International AIDS Vaccine Initiative, New York, NY (US); The Scripps Research Institute, La Jolla, CA (US)

(72) Inventors: Shailendra Kumar Sharma, La Jolla, CA (US); Richard Wyatt, La Jolla, CA (US)

(73) Assignees: International AIDS Vaccine Initiative, New York, NY (US); The Scripps Research Institute, La Jolla, CA (US)

(*) Notice: Subject to any disclaimer, the term of this patent is extended or adjusted under 35 U.S.C. 154(b) by 0 days.

(21) Appl. No.: 15/075,348

(22) Filed: Mar. 21, 2016

(65) Prior Publication Data

US 2016/0279230 A1 Sep. 29, 2016

Related U.S. Application Data

(60) Provisional application No. 62/137,147, filed on Mar. 23, 2015.

(51) Int. Cl.
| | |
|---|---|
| *A61K 39/21* | (2006.01) |
| *C07K 14/005* | (2006.01) |
| *C12N 7/00* | (2006.01) |
| *A61K 39/12* | (2006.01) |
| *C07K 16/10* | (2006.01) |
| *A61K 39/39* | (2006.01) |
| *A61K 39/00* | (2006.01) |

(52) U.S. Cl.
CPC ............... *A61K 39/21* (2013.01); *A61K 39/12* (2013.01); *A61K 39/39* (2013.01); *C12N 7/00* (2013.01); *A61K 2039/55505* (2013.01); *A61K 2039/55511* (2013.01); *A61K 2039/55555* (2013.01); *A61K 2039/55566* (2013.01); *A61K 2039/55577* (2013.01); *A61K 2039/572* (2013.01); *A61K 2039/575* (2013.01); *A61K 2039/645* (2013.01); *C07K 14/005* (2013.01); *C12N 2740/16122* (2013.01); *C12N 2740/16134* (2013.01); *C12N 2740/16171* (2013.01)

(58) Field of Classification Search
CPC .......... A61K 39/21; A61K 2039/55505; A61K 2039/55511; A61K 2039/55555; C12N 7/00
See application file for complete search history.

(56) References Cited

U.S. PATENT DOCUMENTS

| | | |
|---|---|---|
| 2013/0139274 A1 | 5/2013 | Sanders |
| 2014/0212458 A1 | 7/2014 | Caulfield et al. |
| 2016/0188790 A1 | 6/2016 | Dormitzer et al. |

FOREIGN PATENT DOCUMENTS

| | | |
|---|---|---|
| EP | 2 873 423 | 5/2015 |
| WO | 2015/004158 | 1/2015 |

OTHER PUBLICATIONS

European Search Report dated Aug. 12, 2016, which issued during prosecution of European Application No. 16 02 0092.
Kesavardhana, et al. "Stabilizing the Native Trimer of HIV-1 Env by Destabilizing the Heterodimeric Interface of the gp41 Postfusion Six-Helix Bundle" Journal of Virology, Sep. 2014, 88(17):9590-9604.
Kovacs, et al. "Stable, uncleaved HIV-1 envelope glycoprotein gp140 forms a tightly folded timer with a native-like structure" Proceedings of the National Academy of Sciences, Dec. 2014, 111(52):18542-18547.
Sanders, et al. "Stabilization of the Soluble, Cleaved, Trimeric Form of the Envelope Glycoprotein Complex of Human Immunodeficiency Virus Type 1" Journal of Virology, Sep. 2002, 76(17):8875-8889.
Sharma, et al. "Cleavage-Independent HIV-1 Env Trimers Engineered as Soluble Native Spike Mimetics for Vaccine Design" Cell Reports, Apr. 2015, 11(4):539-550.

*Primary Examiner* — Barry A Chestnut
(74) *Attorney, Agent, or Firm* — Vedder Price P.C.; Thomas J. Kowalski; Deborah L. Lu

(57) ABSTRACT

The present application relates to novel HIV-1 envelope glycoproteins which may be utilized as an HIV-1 vaccine immunogens, antigens for crystallization and for the identification of broad neutralizing antibodies. The present invention encompasses the preparation and purification of immunogenic compositions which are formulated into the vaccines of the present invention.

18 Claims, 41 Drawing Sheets
(4 of 41 Drawing Sheet(s) Filed in Color)

Aim: To detect profile changes similar to I559P by new HR1 proline substitutions to generate well-ordered timers in NFL context BG505NFL2 HR1 proline scan: Total 36 residues were mutated to prolines Screening Method: Immunoprecipitation, SEC profile, negative-stain EM, antigenicity study (Octet) and DSC

FIG. 4A

| HR1 Mutations |
|---|
| G547P |
| I548P |
| V549P |
| Q550P |
| Q551P |
| Q552P |
| S553P |
| N544P |
| L555P |
| L556P |
| R557P |
| A558P |
| I559P |
| E560P |
| A561P |
| Q562P |
| Q563P |
| H564P |
| L565P |
| L566P |
| K567P |
| L568P |
| T569P |
| V570P |
| W571P |
| G572P |
| I573P |
| K574P |
| L576P |
| Q577P |
| R579P |
| V580P |
| V583P |
| E584P |
| L587P |
| Y586P |

FIG. 4B

|  | BG505NFL2P (KD in M) | BG505NFL2 L555P (KD in M) |
|---|---|---|
| 2G12 | <1.0E-12 | <1.0E-12 |
| PGT145 | 8.51E-09 | 8.98E-09 |
| PGT151 | 7.4E-09 | 4.2E-09 |
| PGDM1400 | 10.6E-09 | 0.6E-09 |

FIG. 7B

JRFL Native Flexibly Linked well-ordered trimers arrayed on liposomes

JRFL gp140-NFL2P

Trimers ~ 10-15 nm apart...

Should impart avidity gain

- Thermal stability (37°C)
- B cell activation *in vitro* cell lines
- Immunogenicity

* Covalent cysteine linkage, NFL-Cys

FIG. 10

NFL2 linker position in the BG505 SOSIP structure and the
BG505-NFL2 negative stain 3D reconstruction

FIG. 11

Single mutations involving only HR1 residues

| | 2G12 | VRC06 | PGT145 | PGT151 | F105 | 19b |
|---|---|---|---|---|---|---|
| 16055_I544P | ++ | - | +/- | - | + | ++ |
| 16055_V549P | ++ | - | +/- | - | + | ++ |
| 16055_Q551P | ++ | +/- | +/- | - | +++ | +++ |
| 16055_L555P | ++ | + | ++ | + | +++ | +++ |
| 16055_L556P | ++ | +/- | +/- | - | +++ | +++ |
| 16055_A558P | ++ | +/- | +/- | - | +++ | +++ |
| 16055_I559P | ++ | +/- | ++ | + | ++ | n.d. |
| 16055_Q562P | ++ | + | + | +/- | +++ | +++ |
| 16055_Q563P | ++ | + | ++ | +/- | ++ | ++ |
| 16055_L565P | ++ | + | ++ | +/- | ++ | ++ |
| 16055_L566P | ++ | + | ++ | +/- | ++ | ++ |
| 16055_L568P | ++ | + | ++ | + | ++ | + |
| 16055_T569P | ++ | + | ++ | + | ++ | + |
| 16055_V570P | | | | | | |
| 16055_K571P | | | | | | |
| 16055_G572P | | | | | | |
| 16055_I573P | | | | | | |
| 16055_K574P | | | | | | |
| 16055_L575P | | | | | | |
| 16055_Q577P | | | | | | |
| 16055_R578P | | | | | | |
| 16055_V580P | | | | | | |
| 16055_V581P | | | | | | |
| 16055_E584P | | | | | | |
| 16055_V585P | | | | | | |
| 16055_L587P | | | | | | |
| 16055_S649P | ++ | +/- | +/- | - | +++ | +++ |

Color coding: POSITIVE / NEGATIVE / IN PROGRESS

FIG. 16

| MUTANT | 2G12 | PGT145 | F105 |
|---|---|---|---|
| 16055 I559P S649D | ++ | +/- | ++ |
| 16055 L555P S649D | ++ | +/- | ++ |
| 16055 A558P S649D | ++ | +/- | +++ |
| 16055 I559P S649D | ++ | + | ++ |
| 16055 L555P S649E | ++ | + | ++ |
| 16055 L555P S649E | ++ | +/- | +/- |
| 16055 A558P S649E | ++ | + | +++ |
| 16055 I559P S649E | +++ | ++ | +++ |
| JRFL I559P S649D | ++ | + | + |
| JRFL I559P S649E | ++ | ++ | + |
| JRFL WT S649D | ++ | - | + |
| JRFL WT S649E | ++ | - | + |

FIG. 18

| |
|---|
| G547P |
| I548P |
| V549P |
| Q550P |
| Q551P |
| Q552P |
| N553P |
| N554P |
| L555P |
| L556P |
| R557P |
| A558P |
| I559P |
| E560P |
| A561P |
| Q562P |
| Q563P |
| R564P |
| M565P |
| L566P |
| Q567P |
| L568P |
| T569P |
| V570P |
| W571P |
| G572P |
| I573P |
| K574P |
| Q575P |
| L576P |
| Q577P |
| R579P |
| V580P |
| V583P |
| E584P |
| Y586P |
| L587P |

FIG. 21A

|         | 2G12 | VRC06 | PGT145 | PGT151 | F105 | 19b |
|---------|------|-------|--------|--------|------|-----|
| JRFL I559P | ++ | + | ++ | + | ++ | ++ |
| JRFL I564P | ++ | ++ | ++ | + | ++ | + |
| JRFL I635P | ++ | +/- | ++ | + | ++ | + |
| JRFL I657P | ++ | + | ++ | + | ++ | ++ |
| JRFL I660P | ++ | + | ++ | + | ++ | ++ |

FIG. 21B

|         | 2G12 | VRC06 | PGT145 | PGT151 | F105 | 19b |
|---------|------|-------|--------|--------|------|-----|
| JRFL I559P | ++ | + | ++ | + | ++ | ++ |
| JRFL I564P | ++ | ++ | ++ | + | ++ | + |
| JRFL I635P | ++ | +/- | ++ | + | ++ | + |
| JRFL I657P | ++ | + | ++ | + | ++ | ++ |
| JRFL I660P | ++ | + | ++ | + | ++ | ++ |

FIG. 21C

FIG. 23A
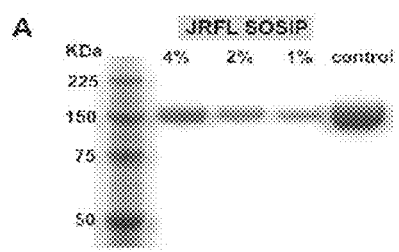 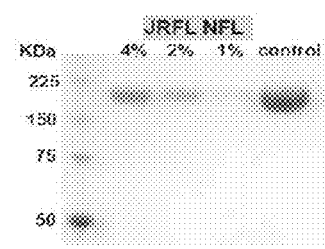
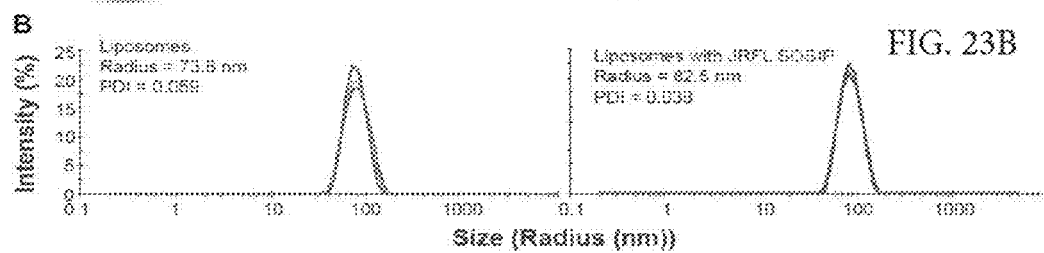
FIG. 23B
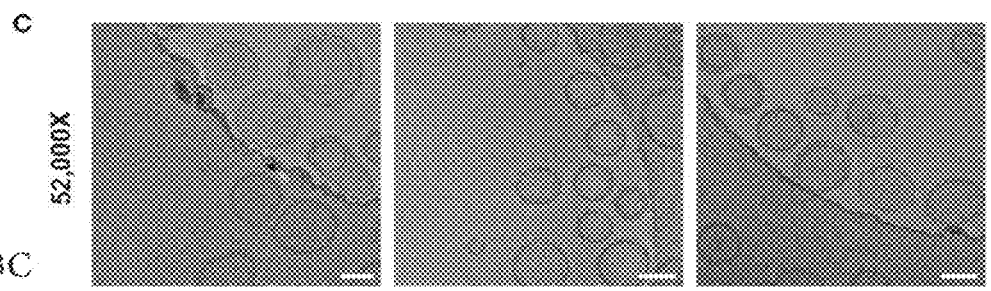
FIG. 23C

FIG. 24A
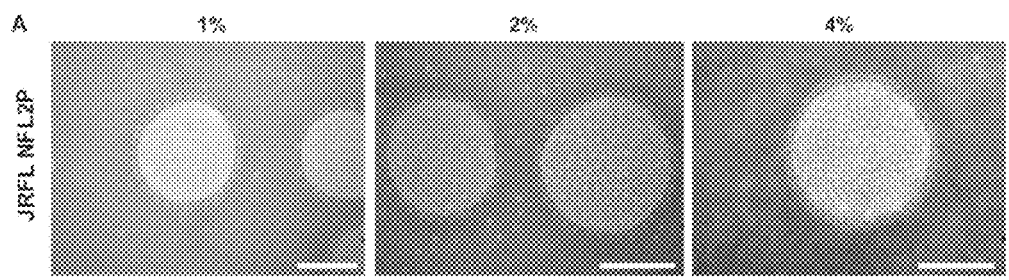
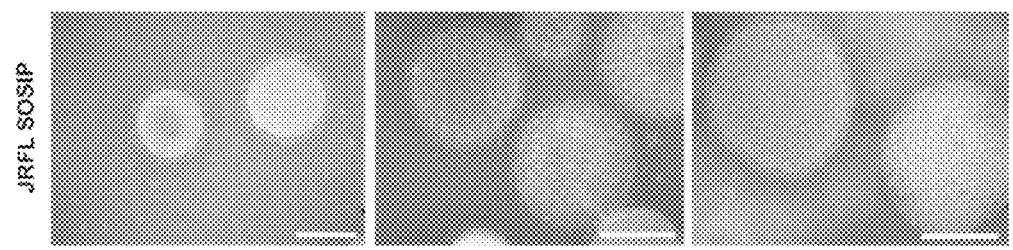
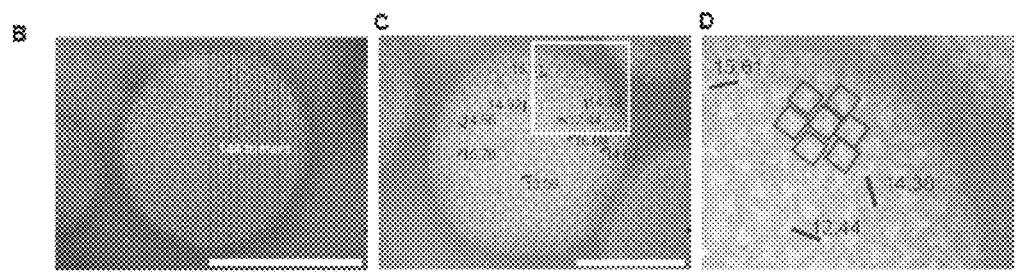
FIG. 24B    FIG. 24C    FIG. 24D

FIG. 26A
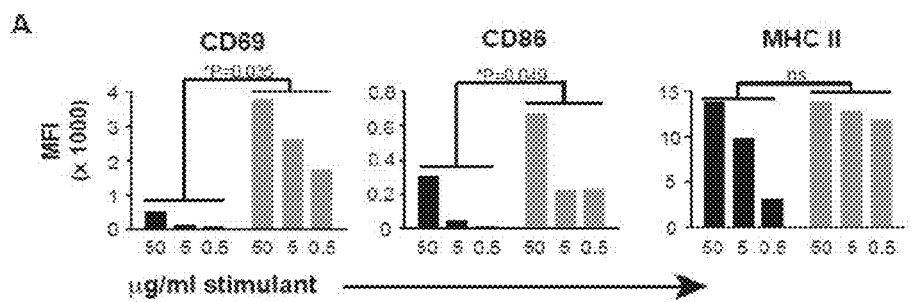
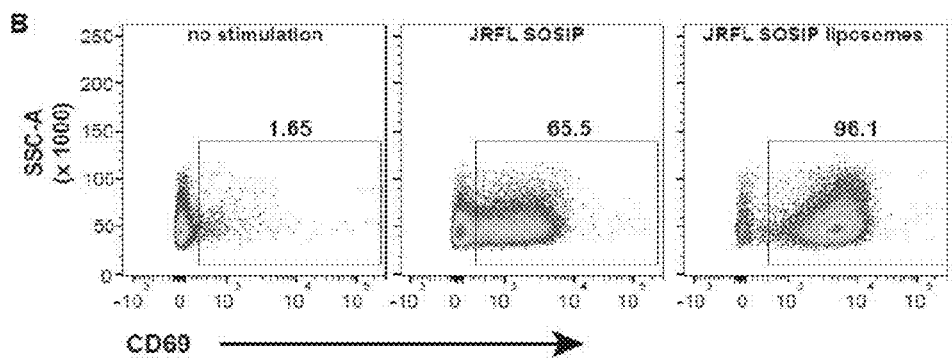
FIG. 26B
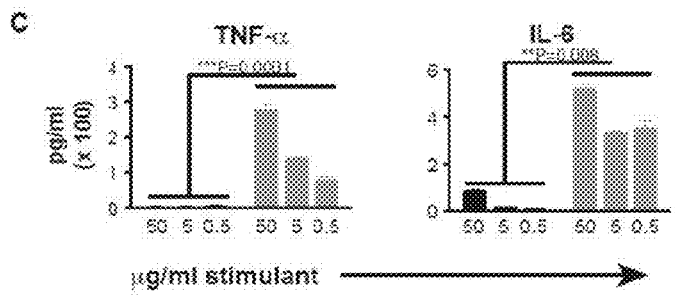
FIG. 26C
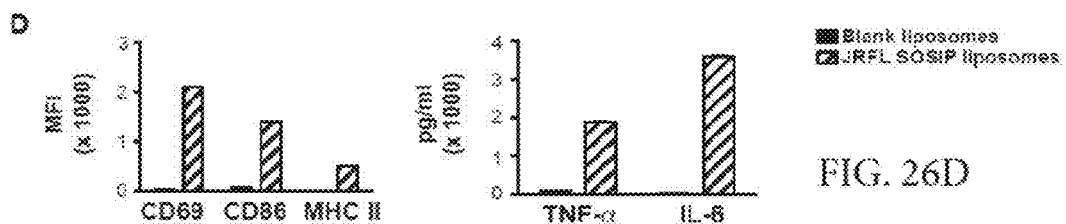
FIG. 26D

FIG. 28A
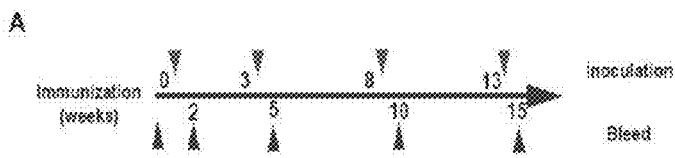
FIG. 28B
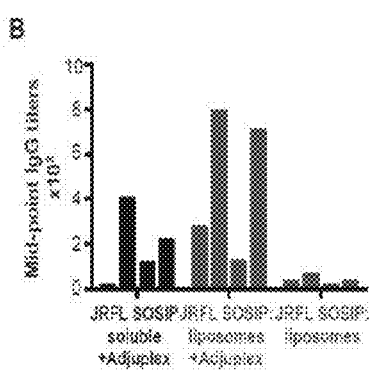
FIG. 28C
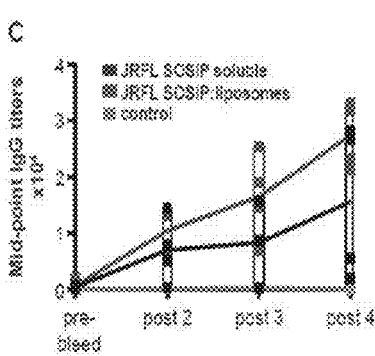
FIG. 28D
FIG. 28E
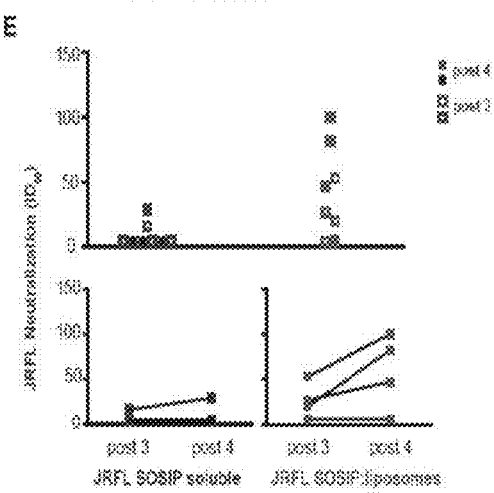

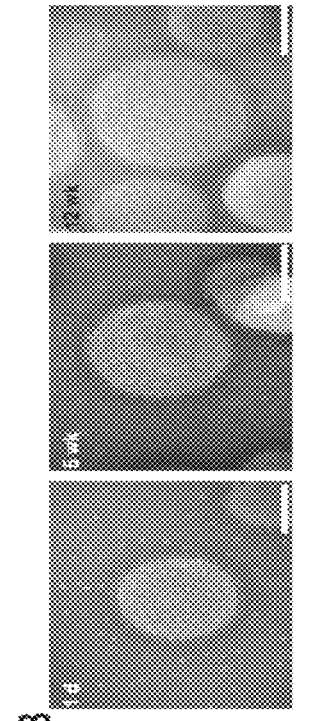
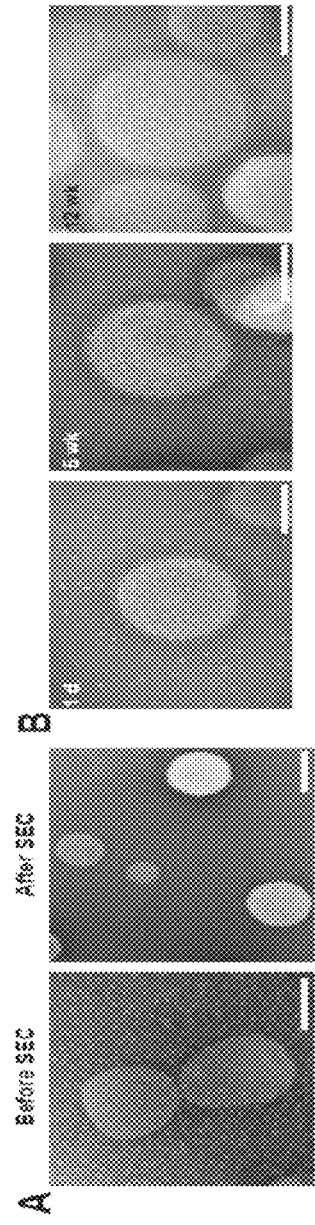
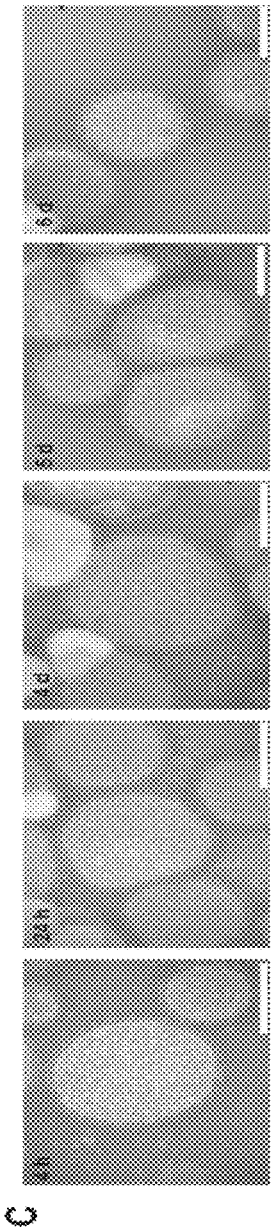
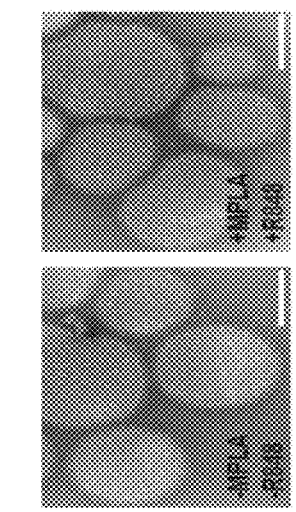
FIG. 30A  FIG. 30B  FIG. 30C  FIG. 30D  FIG. 30E FIG. 31A
FIG. 31B
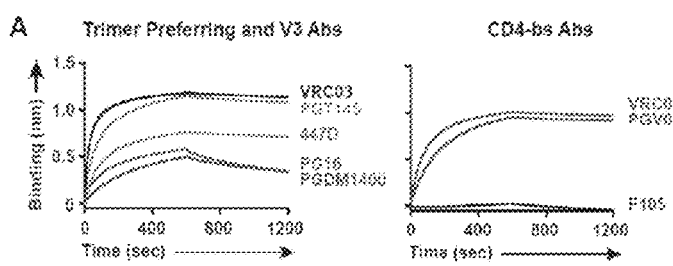
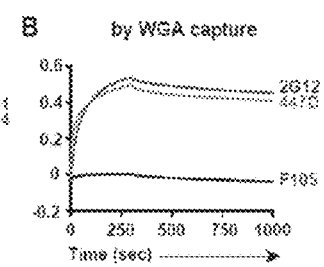
FIG. 31C
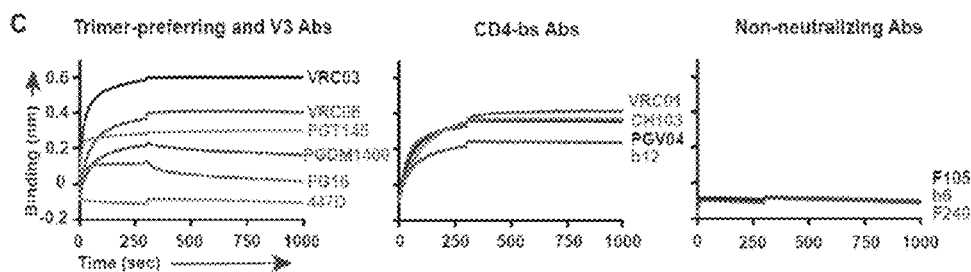
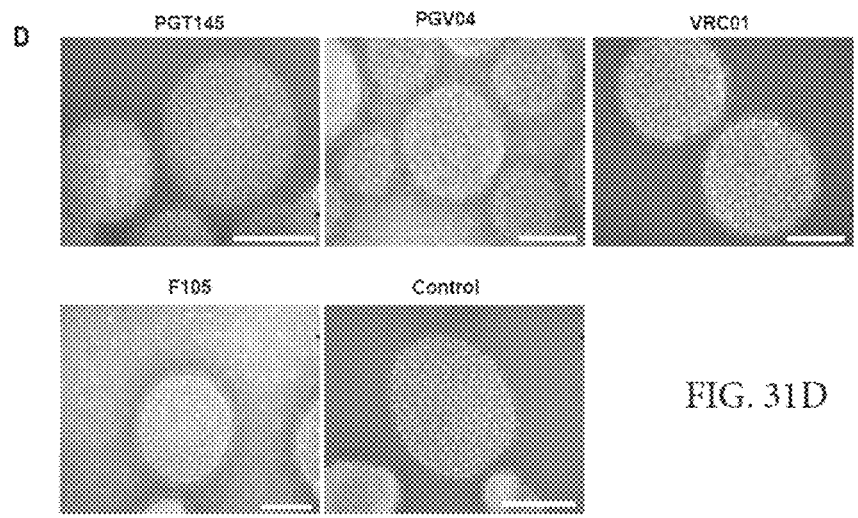
FIG. 31D

SOLUBLE HIV-1 ENVELOPE GLYCOPROTEIN TRIMERS

RELATED APPLICATIONS AND/OR INCORPORATION BY REFERENCE

This application claims benefit of and priority to U.S. provisional patent application Ser. No. 62/137,147 filed Mar. 23, 2015.

Reference is made to U.S. patent application Ser. No. 14/508,369 filed Oct. 7, 2014 which claims priority to U.S. provisional patent application Ser. No. 62/054,727 filed Sep. 24, 2014, 62/032,507 filed Aug. 1, 2014, 61/941,101 filed Feb. 18, 2014 and 61/887,618 filed Oct. 7, 2013.

Reference is also made to international patent application Serial No. PCT/US11/26862 filed Mar. 2, 2011 which published as international patent publication WO 2011/109511 on Sep. 9, 2011 and claims priority to U.S. provisional patent application Ser. No. 61/309,685 filed Mar. 2, 2010. Reference is also made to U.S. provisional patent application Ser. No. 61/664,990 and 61/722,739 filed Jun. 27, 2012 and Nov. 5, 2012, respectively.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This application relates to a novel HIV-1 envelope glycoprotein which may be utilized as an HIV-1 vaccine immunogen, as a native Env trimer mimic, for identification of small molecules for use as immunogen that bind specific HIV-1 broad neutralizing antibodies, for identification of small molecules for use as anti-viral compound that bind specific HIV-1 envelope glycoprotein monomer and/or trimer, as antigens for crystallization and electron microscopy (EM) structural analysis and for the identification of broad neutralizing antibodies from HIV-1 infected individuals or vaccinated subjects or antibody or ligand libraries.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4$^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4$^+$ T-lymphocytes, which are critical to immune defense, is a major cause of the progressive immune dysfunction that is the hallmark of AIDS disease progression. The loss of CD4$^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 June 19; 280(5371):1884-8). For fusion with its target cells, HIV-1 uses a trimeric Env complex containing gp120 and gp41 subunits (Burton et al., Nat Immunol. 2004 March; 5 (3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been daunting task (Phogat S, Wyatt R. Curr Pharm Des. 2007; 13:213-27, Phogat S, et al. J Intern Med. 2007 262:26-43, Karlsson Hedestam G B, et al Nat Rev Microbiol. 2008 6:143-55).

The ability to elicit broad and potent neutralizing antibodies is a major challenge in the development of an HIV-1 vaccine. Namely, HIV-1 has evolved an impressive array of strategies to evade antibody-mediated neutralization, bNAbs develop over time in a proportion of HIV-1 infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, due to the ability of these bNabs to recognize conserved recessed targets on HIV Env which are either inaccessible by elicited antibodies or difficult to precisely redesign and present to the immune system.

Recently using a sensitive high-throughput micro-neutralization screening of supernatants from approximately 30,000 IgG+ memory B cells from a HIV-1 clade A-infected African donor, Applicants identified two new bNabs PG9 and PG16 that are broad and exceptionally potent neutralizing antibodies (Walker L, Phogat S, et al. Science. 2009; 326:285-9. Epub 2009 Sep. 3). These antibodies recognize a new conserved, yet accessible, vaccine target (consisting of conserved elements on the variable loops 2 and 3) on the Env and show preferential binding to HIV Env trimer (Model of PG9 and 16 epitopes on HIV-1 trimer.). When tested for binding, these antibodies did not show binding to many empirically designed soluble (Env gp140) HIV Env trimer thought to be mimics of the native HIV-1 Env spike, suggesting that either these Env designs are either incorrect or they are fixed in a form not recognized by PG9 and PG16.

Citation or identification of any document in this application is not an admission that such document is available as prior art to the present invention.

SUMMARY OF THE INVENTION

The present invention encompasses mutations of 36 residues from HR1 that are individually mutated to proline (see, e.g., FIGS. 4A and 4B) in a Clade A (such as BG505-NFL2) trimer. Octet binding data and EM suggest L555P, L556P, and A558P are other prolines similar to I559P (see, e.g., FIG. 6). In particular, L555P was recognized efficiently by bNAbs and trimer-preferring bNAbs (see, e.g., FIG. 7). In an advantageous embodiment, preferred mutations include, but are not limited to, S553P, N554P, L555P, E560P, Q562P, Q563P or any combination thereof.

The present invention encompasses mutations of residues from HR1 that stabilize a clade C (such as 16055-NFL2) trimer. (see, e.g., FIG. 16). In an advantageous embodiment, preferred mutations include, but are not limited to, L555P, Q652P, Q653P, L565P, L566P or any combination thereof.

The present invention encompasses mutations of residues from HR1 that stabilize a Clade B (such as JRFL-NFL2) trimer. (see, e.g., FIG. 21). In an advantageous embodiment, preferred mutations include, but are not limited to, L555P, N554P, I559P, Q562P, Q563P, S649D or any combination thereof.

Another embodiment of the present invention encompasses methods of eliciting an immune response which may comprise administering to a mammal the any of the trimers disclosed herein. The method may further comprise adding an adjuvant. The adjuvant may be a lecithin and may optionally be combined with an acrylic polymer, a lecithin coated oil droplet in an oil-in-water emulsion or a lecithin and an acrylic polymer in an oil-in-water emulsion. The adjuvant may be ISCOMATRIX or Adjuplex. In another embodiment, the adjuvant may comprise alum.

In another embodiment, the trimer may be administered in a liposome or a nanoparticle. In another embodiment, the trimer may be fixed, for example, in glutaraldehyde.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIGS. 4A-B depict a BG505 NFL HR1 proline scan.

FIGS. 7A-B shows that BG505NFL2 L555 is recognized efficiently by bNAbs and trimer-preferring bNAbs.

FIG. 10 depicts JRFL native flexibly linked well-ordered trimers arrayed on liposomes.

FIG. 11 depicts an NFL2 linker position in the BG505 SOSIP structure and the BG505-NFL2 negative stain 3D reconstruction.

FIG. 16 depicts a summary of the HR1 proline screen in the 16055 gp140-NFL2 construct: based on the initial immunoprecipitation and initial octet binding data.

FIG. 18 depicts 7 positive HR2 double mutants confirmed by IP results.

FIGS. 21A-C depict 5 positive hits in JRFLNFL2 and 1 positive hit in JRFLNFL2 in the HR2 region as S649D mutation.

FIGS. 23A-C depict characterization of JRFL SOSIP-conjugated liposomes. (A) Reducing SDS PAGE of 4%, 2% and 1% Ni DGS-NTA(Ni) JRFL SOSIP and JRFL NFL trimer-conjugated liposomes. JRFL SOSIP and JRFL NFL2P soluble trimeric glycoproteins are included as controls. (B) Dynamic light scattering (DLS) of the 4% DGS-NTA(Ni) liposomes and JRFL SOSIP-conjugated liposomes was performed using a using Zetasizer Nano instrument to measure particle size and the polydispersity index. (C) Cryo-EM images of 4% Ni JRFL SOSIP liposomes at 52,000 and 110,000× magnification. Scale bar=100 nm. See also FIG. 29.

FIGS. 24A-D depict incorporation of different amounts of DGS-NTA(Ni) into the liposomes to increase JRFL trimer density on the liposomal surface. Negative stain EM images of DGS-NTA(Ni) liposomes made with 1%, 2% and 4% DGS-NTA(Ni) and conjugated with either JRFL NFL or JRFL SOSIP trimers. All images are at 18,000× magnification. Scale bar=100 nm. (B) Representative negative stain image of 4% JRFL SOSIP-conjugated liposomes with a counting grid (red lines) to manually determine the approximate number of trimers visible in half the area of the trimer-liposome image. (C) Measurement of distances (nm) between selected trimers as demarked by blue bars, center to center. Numbers indicate the distance between the two adjacent trimers. (D) Zoomed image of the white square area from panel C. See also FIG. 30.

FIGS. 26A-D depict activation of primary B cells by soluble JRFL SOSIP trimers and JRFL SOSIP trimer-conjugated liposomes. B cells from b12 mature knock-in mice were negatively selected from splenocytes and induced by overnight incubation with either soluble JRFL SOSIP trimers or 4% liposomes conjugated with JRFL SOSIP trimers. The cell-surface activation markers and the cytokines secreted by the activated cells were analyzed by cell-surface staining or ELISA. (A) FACS staining of cell-surface activation markers plotted as MFI values. Soluble JRFL SOSIP (black); JRFL SOSIP conjugated to liposomes (grey bars). (B) Frequency of CD69+ cells upon activation by 50 µg/ml of soluble trimers or JRFL SOSIP trimer-conjugated liposomes. (C) TNF-α and IL-6 levels present in the supernatants of the B-cells upon overnight activation by soluble JRFL SOSIP trimers (black bars) or JRFL trimer-conjugated liposomes (grey bars) B cells were assessed. (D) MFI values of cell surface activation markers and levels of cytokines produced by B cells upon activation by 50 µg/ml of JRFL SOSIP liposomes or similar dilution of blank liposomes without any trimers on the surface. Statistical comparisons between groups are performed by paired t-test. See also FIG. 32.

FIGS. 28A-E depict immunogenicity of the JRFL SOSIP trimer-conjugated liposomes. (A) Timeline of inoculations and bleeds. Bleeds were collected 2 weeks after each injection. (B) Mid-point IgG titers of individual rabbits immunized 3 times with 25 ug JRFL SOSIP protein as soluble trimers or conjugated to liposomes in the presence or absence of exogenous adjuvant Adjuplex were determined. Sera were collected 2 weeks after the 3rd injection and were analyzed by ELISA with JRFL SOSIP trimers captured on ELISA plate via the C-terminal His6tag. (C) Mid-point IgG titers of rabbits immunized 4 times with JRFL SOSIP soluble protein or JRFL SOSIP conjugated to liposomes. ELISA plates were coated with anti-His monoclonal antibody to capture JRFL SOSIP trimers via the C-terminal His6-tag. (D) Neutralization ID50 values of SF162, HxBc2, and JRFL viruses by antisera following the third and fourth inoculations. Control animals were inoculated with blank liposomes in Adjuplex. (E) Combined JRFL neutralization ID50 values elicited by the soluble trimers compared to the trimer-conjugated liposomes are plotted after third and fourth inoculations. Lower panel shows boosts in ID50 values after the fourth inoculation for both group of rabbits. See also FIG. 33.

FIGS. 30A-E depict conjugation specificity and stability of liposomes. (A) Representative negative stain EM images of DGPC liposomes with no DGS-NTA(Ni) mixed with JRFL SOSIP trimer before and after size exclusion chromatography. (B) 2% DGS-NTA(Ni) liposomes with JRFL NFL trimeric protein were incubated at 4° C. or (C) 37° C. for varying times as indicated on the images and stained by phospho-tungstate for EM analysis. (D) 4% Ni DGPC liposomes with JRFL SOSIP trimeric protein were mixed and incubated at 37° C. for 1 hour with Iscomatrix or Adjuplex and stained by phospho tungstate for EM analysis. Red arrows indicate the adjuvant in both cases. (E) 4% Ni DGPC liposomes without and with MPLA and R848 conjugated with JRFL SOSIP trimers. Scale bar=100 nm.

FIGS. 31A-D depict binding of HIV-1 antibodies to soluble JRFL SOSIP and liposome bound JRFL NFL. Binding of anti-HIV-1 monoclonal antibodies assessed by Bio-Layer Interferometry (BLI) using Octet. (A) Monoclonal antibodies were immobilized on human anti-Fc sensors and soluble JRFL SOSIP protein was used as an analyte. (B) JRFL NFL (10 µg/ml) was immobilized on WGA-captured streptavidin sensors and 20 µg/ml monoclonal antibodies (IgGs) were used as analyte. (C) 4% NTA-Ni liposomes (equivalent to 75 nmoles of phospholipids) conjugated to JRFL NFL were immobilized on WGA-captured streptavidin sensors and 20 µg/ml monoclonal antibodies (IgGs) were used as analyte. (D) 2% NTA-Ni liposomes with JRFL NFL were incubated with 10 molar excess of respective antibodies (IgG) at 37° C. for 30 min and stained with phospho tungstate and viewed by EM. All images are at 180,000 magnification. Scale bar=100 nm.

DETAILED DESCRIPTION

Figure 1:
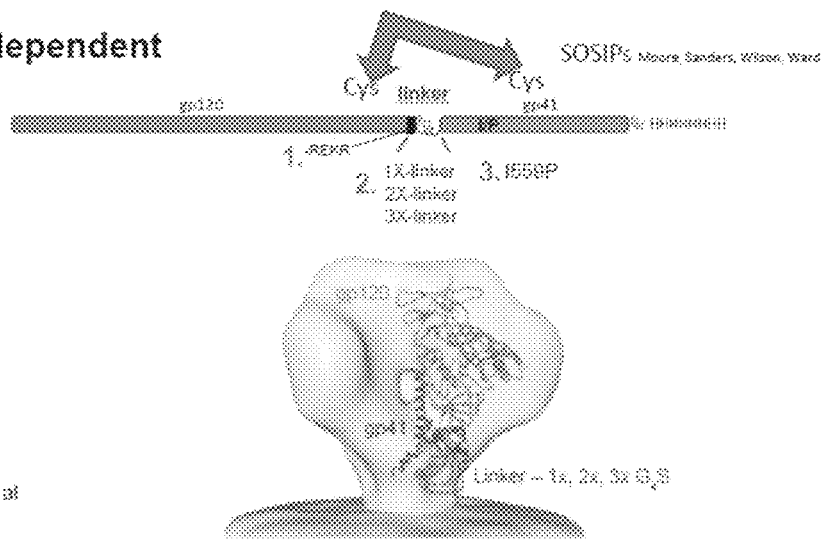
FIG. 1 depicts native flexibily linked (NFL) gp140 trimers.
Figure 2:
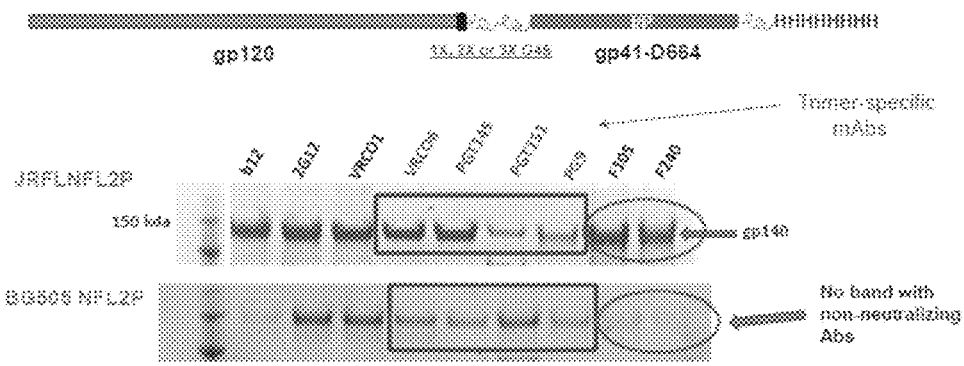
FIG. 2 depicts an IP screen of uncleaved NFL trimers with a 10 residue flexible linker optimal.
Figure 3:
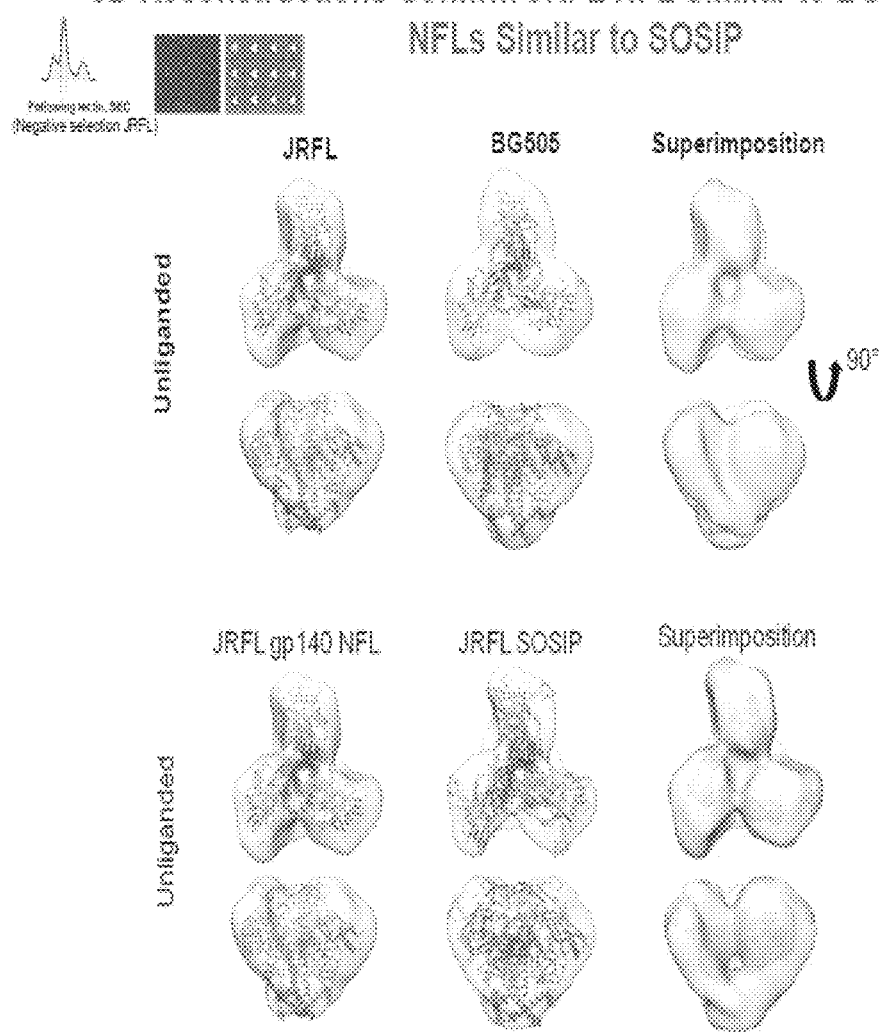
FIG. 3 depicts 3D reconstructions that confirm JRFL NFL similar to BG505 NFL and NFLs similar to SOSIP.
Figure 5:
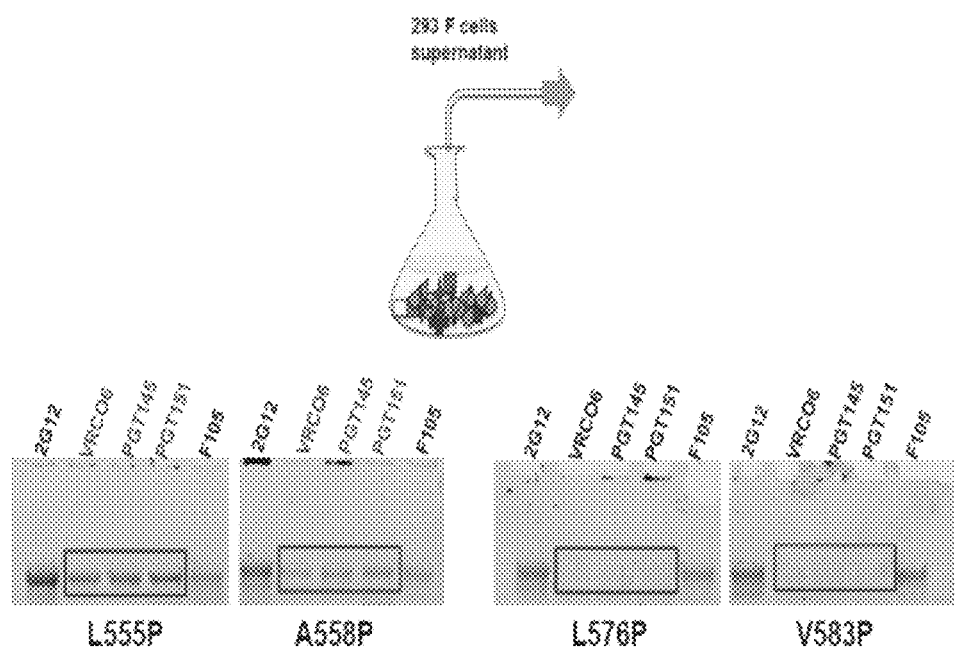
FIG. 5 depicts immunoprecipitations that indicate that L555P and A558P are making well-ordered NFL trimers.

The present invention relates to stabilizing clade A (such as BG505), Clade B (such as JR-FL) and clade C (such as 16055) Env trimers in their native-like conformation in a NFL platform. The present invention also relates to determining a common proline mutation that can be easily translated to stabilize majority of the ENV trimers spanning different clades.

Without being bound by limitation, in the native spike, the gp41 subunit exists in a metastable conformation and it favorably forms a stable post-fusion six-helix bundle (6HB), which is composed of trimers of HR1 (N-heptad repeat) and HR2 C-heptad repeat) heterodimers facilitating the fusion of HIV with the host CD4 T cells. The formation the 6HB is a irreversible process destabilizing the native trimer resulting in exposure of immunodominant and non-neutralizing epitopes to the immune system. Ideally, any mutation in the HR1 or HR2 that can destabilize the 6HB formation will stabilize the ENV trimers in native-like conformation.

Soluble, stabilized, proteolytically cleaved, trimeric gp41 proteins can be generated by engineering an intermolecular disulphide bond between gp120 and gp41 (SOS), combined with a single residue change, I559P, within gp41 (SOSIP). Applicants have developed a purification method of homogenous trimers from a mixture of trimers derived from the JRFL clade B virus strain Env. These trimers, known as JRFL SOSIPs may comprise a cysteine pair covalently linking gp120 to gp41, a poly R cleavage site, MPER deletion, a 168 E/K change or a combination thereof. The purification method is scalable, avoids the published 2G12 monoclonal antibody column purification and employs antibody-mediated negative selection to rescue JRFL SOSIP trimers from a heterogenous mixture of trimers in different and 'random' conformation to a high degree of conformational and structural homogeneity, which is expandable to other strains and clades of HIV.

The present invention also encompasses SOSIP trimer molecules derived from the B subtype strain, JRFL, and the subtype C strain, 16055. Applicants selected these two Envs for the initial results reported in this study as follows. The JRFL SOSIP trimer, truncated at residue 663 (JRFL SOSIP 663) derives from the JRFL HIV-1 strain isolated from the frontal lobe (FL) of an HIV-1-infected individual. This Env is often used because it displays the unusual property that its gp160 Env precursor is efficiently cleaved into the gp120 and gp41 subunits when expressed on the cell surface of 293F HEK cells (Pancera M & Wyatt R (2005) Virology 332(1):145-156). The 16055 SOSIP.663 trimer, also truncated at residue 663, derives from a HIV-1 Indian strain and displays the unusual property that its monomeric gp120 is recognized by the quaternary epitope-preferring bNAbs, PG9 and PG16, which is relatively infrequent amongst most HIV-1 Env sequences (McLellan J S, et al. (2011) Nature 480(7377):336-343), and is also observed for BG505 gp120 (Julien J P, et al. (2013) Proc Natl Acad Sci USA 110(11): 4351-4356; Hoffenberg S, et al. (2013) J Virol 87(10):5372-5383).

Applicants have designed and purified HIV gp145 trimers possessing a hydrophilic transmembrane region re-engineered from the previously hydrophobic TM. This allows secretion of either uncleaved or cleaved gp145 trimers, not previously possible. This should be expandable to other strains and clades of HIV.

Applicants have designed and developed HIV gp120 trimers stabilized by engineered variable region cysteine pairs and by appending a heterologous trimerization motif selected from the pdb.

Applciants have also designed and developed a new method to produce soluble, fully uncleaved, homogeneous, highly stable gp140s trimers as a native spike mimetics. In this method the native-likegp120 subunit is covalently linked to gp41 via peptide based flexible linkers and the method is easily expandable to other strains and clades of HIV.

The SOSIP envelope glycoproteins identified as a part of this invention show significantly better binding to new identified broad neutralizing antibodies PG9 and/or PG16 and are well recognized by all known broadly neutralizing antibodies (bNAbs). The JRFL HPTMs and gp120 MIFs may be recognized by trimer-specific bNabs and likely recognized by bNAbs of other specificities. The envelope glycoproteins Envs have value (a) as reagents for screening of broad neutralizing antibodies (bNAbs), such as but not limited to, PG9 and PG16, the PGT145 family, the PGT128 family and for the SOSIPs the VRC01-like mabs including VRC06, (b) as reagents for screening of small molecules that compete binding of broad neutralizing antibodies, such as but not limited to, PG9 and PG16, (c) as monomer and native envelope trimer mimic for crystallization studies and (d) as immunogens in different forms to use as HIV-1 vaccine components, for example, to elicit broadly neutralizing antibodies.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus. In an advantageous embodiment, the soluble envelope glycoproteins of the present invention may be isolated from the 6535 virus, the 13095 virus, the 16055 virus, the 25710 virus, the 25925 virus, the CAAN virus, the BG505 virus or the Zm109F virus.

In a particularly advantageous embodiment, the trimer protein, is prepared, purified and formulated for immunization in a human.

In another particularly advantageous embodiment, the trimer protein, is formulated for immunization in a human to contain an adjuvant. A number of adjuvants are well known to those investigating vaccines but could include but are not limited to those containing alum.

In another particularly advantageous embodiment, the trimer protein is further attached to a particle such that multiple copies of the trimer are attached and this material is prepared and formulated for immunization in a human.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or the specification.

Another advantageous embodiment encompasses a stable soluble HIV-1 envelope glycoprotein trimer mimic.

Applicants have designed completely new gp120 and gp145 trimers based upon the cryo-EM densities of the HIV-1 functional spike, as well as based upon Applicants' means of producing and purifying JRFL SOSIP trimers (residue 168 E to K modified for PG9/16 recognition) to a high degree of homogeneity. For gp120 trimer de novo design, using SOSIP EM structures, and Applicants' densities, Applicants have appended new trimer motifs completing replacing gp41 (and the need for cleavage) in combination with structure-guided cysteine pairs to lock down the metastable variable (V) loops on gp120.

Using this design strategy, Applicants have generated gp120 trimers that express well, appear trimeric by EM, and are efficiently recognized preferentially by the broadly neutralizing mAbs as opposed to non-neutralizing mAbs.

Applicants have very recently successfully produced gp145 trimers that contain the entire ectodomains of gp120 and gp41 by modifying the usually hydrophobic transmembrane (TM) region to be hydrophilic and allowing secretion rather than membrane attachment. Applicants have made several by systematic TM deletions and site directed, sequence specific N-glycan additions.

To a varying degree, and especially for the JRFL SOSIPs, all three of these trimers display the epitopes of virtually all the broadly neutralizing HIV-1 mAbs, including the extremely potent, glycan-dependent PGT mAbs. An objective of the present invention is to render all three trimers with these recognition properties.

Second generation soluble trimers display desired structural features and antigenic profile. They are used as immunogens in animal models to elicit improved neutralizing antibodies. The soluble trimers are assessed in combination with the ability of genetic Env trimer expression to prime (or boost) neutralizing antibody responses to HIV-1 Env. The influence of trimer modifications using previous analyses of trimer-elicited responses in NHPs directed toward the CD4bs are pursued in parallel to improve the elicitation of neutralizing antibodies. Recent analysis of trimer-elicited CD4bs-directed mAbs indicates that they approach the HIV spike "from the top" rather than accessing the CD4bs "from the side" as do the broadly neutralizing mAbs such as VRC01 and PGV04, dictating immunogen re-design (manuscript in Appendix). In addition, the commonly elicited NHP CD4bs mAbs possess hydrophobic HCDR3s which often interact with the Phe 43 cavity, indicating that filling of this cavity with less hydrophobic residues should be revisited for immunogen modification in either the 1st generation or the future generations of trimer design and development.

Due to the structural limitations of the first generation gp140 foldon trimers and their inability so far to elicit broadly neutralizing antibodies, Applicants designed native-like gp140 trimers in which gp120 is covalently attached to gp41 via a peptide flexible linker (native flexible linker trimers termed gp140-NFL). Applicants developed this new trimer design pathway to make soluble mimetics of the native HIV-1 envelope glycoprotein spike for structural, biophysical and antigenic analysis. A subset of these new trimers that are well-ordered and present trimer-specific neutralizing determinants as HIV vaccine candidates to elicit neutralizing antibodies. Applicants expanded these initial designs to clade C and A virus-derived envelope glycoproteins, and to assess these trimers as soluble immunogens. Applicants also assess immunogenicity of these trimers by particulate, high-density array on liposomes or other particles already under development. In one non-limiting example, nickel chromatography may be accomplished with nickel containing lipids in the formulation at 1-2% and then capturing a His6-tagged trimer by nickel chelation.

Applicants designed the native, flexible linked (NFL) trimers by appending a flexible linker between gp120 and gp4 and are optimizing their design. The rationale was to provide flexibility at the cleavage site to allow native rearrangement of gp120 and gp41 trimeric subunits: as it happens after cleavage by furin. The linker used was $G_4S$ with 1, 2 and 3× repeats. The MPER is deleted at position 664 as per SOSIP (for better expression) The trimers have an E168K mutation to potentially restore PG9/16 recognition and I559P mutation to increase the trimer stability. There is no exogenous trimerization domain or foldon or other stabilizing mutations. The vector is a CMV-driven expression vector.

Initially Applicants inserted G4S (glycin/serine) linkers of three different lengths between gp120 and gp41, deleting 4 residues (REKR) at the gp120 C-terminus that comprise the normal furin cleavage site. The strategy is by covalent linker attachment, this will allow the gp120 and gp41 subunits to assume their natural trimeric association that approximates the HIV functional spike. Leveraging off the screening and purification procedures developed with the JRFL SOSIPs, Applicants expressed the gp140-NFL trimers following transient transfection of 293 HEK cells, secretion into serum-free media, and then purified the NFL trimers by lectin chromatography, size exclusion chromatography and F105-based affinity column negative selection.

Immunogens in different forms to use as HIV-1 vaccine components to elicit bNabs. The different forms of the HIV-1 envelope are used in a prime, as DNA/vector expressing the protein/protein and as a boost as protein. The envelopes could also be used as particulate immunogen by cross linking to virus particles like Qbeta, cow pea mosaic virus, CRM, HPV, HBsAg etc.

In an advantageous embodiment, the soluble envelope glycoproteins of the present invention may be isolated from HIV-1 Clade A virus, HIV-1 Clade B virus, HIV-1 Clade C virus, a HIV-1 Clade A pseudo-virus, HIV-1 Clade B pseudo-virus or a HIV-1 Clade C pseudo-virus In an advantageous embodiment, the soluble envelope glycoproteins of the present invention may be isolated from the 6535 virus, the 13095 virus, the 16055 virus, the 25710 virus, the 25925 virus, the CAAN virus or the Zm109F virus.

HIV type 1 (HIV-1) envelope is a noncovalent trimer of gp120-gp41 heterodimers, and its lability has hindered structural studies. SOSIP gp140 is a soluble, proteolytically mature form of the HIV-1 envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 June; 23(6):817-28. Following initial purification, the only significant contaminant was higher-order gp140 aggregates; however, 0.05% Tween 20 quantitatively converted these aggregates into trimers. The surfactant effect was rapid, dose dependent, and similarly effective for a subtype B SOSIP gp140. Surfactant-treated SOSIP gp140 retained favorable antigenicity and formed compact trimers 12-13 nm in size as determined by electron microscopy. Iyer S P et al., AIDS Res Hum Retroviruses. 2007 June; 23(6):817-28 provides a description of homogeneous, cleaved HIV-1 envelope trimers. These proteins may be useful as vaccine immunogens and for studying structure-function relationships within the HIV-1 envelope glycoproteins.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-1 strain KNH1144 form particularly homogenous trimers compared to a prototypic strain (JR-FL, subtype B). Described in U.S. Pat. No. 7,939,083 are the determinants of this enhanced stability which are located in the N-terminal region of KNH11144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

The structure of BG505 gp140 SOSIP, a soluble mimic of the native HIV-1 envelope glycoprotein (Env), marks the beginning of new era in Env structure-based immunogen design. Displaying a well-ordered quaternary structure, these subtype A-derived trimers display an excellent antigenic profile, discriminating recognition by broadly neutralizing antibodies (bNAbs) from non-broadly neutralizing antibodies (non-bNAbs), and provide a solid Env-based immunogenic platform starting point. Even with this important advance, obtaining homogeneous well-ordered soluble SOSIP trimers derived from other subtypes remains challenging. Here, Applicants report the "rescue" of homogeneous well-ordered subtype B and C SOSIP trimers from a heterogeneous Env mixture using CD4 binding site-directed (CD4bs) non-bNAbs in a negative-selection purification process. These non-bNAbs recognize the primary receptor CD4bs only on disordered trimers but not on the native Env spike or well-ordered soluble trimers due to steric hindrance. Following negative selection to remove disordered oligomers, Applicants demonstrated recovery of well-ordered, homogeneous trimers by electron microscopy (EM). Applicants obtained 3D EM reconstructions of unliganded trimers, as well as in complex with sCD4, a panel of CD4bs-directed bNAbs, and the cleavage-dependent, trimer-specific bNAb, PGT151. Using bio-layer light interferometry Applicants obtained a full antigenic profile, demonstrating that the well-ordered trimers were avidly recognized by bNAbs and poorly recognized by non-bNAbs. Biophysical characterization was consistent with thermostability of a homogeneous species that could be further stabilized by specific bNAbs. Applicants establish a new means to obtain soluble Env mimetics derived from both subtypes B and C for expanded use as candidate vaccine immunogens.

This study presents an artful means using HIV non-broadly neutralizing antibodies to isolate new well-ordered trimers engineered to mimic the virus surface protein. These soluble spike mimetics, called SOSIPs, derive from different genetic HIV subtypes B and C, and complement the recently described subtype A-derived BG505 SOSIP. The comprehensive biochemical analysis presented demonstrates that these new homogeneous soluble trimers are faithful mimics of the HIV spike and more importantly provides a novel means to purify a wider array of soluble Env trimers for future structural and immunogenicity studies. Possessing soluble and stable mimics of the HIV spike derived from diverse strains will improve both Applicants' knowledge of HIV spike architecture and extend the geographical/genetic coverage of future vaccine candidates.

The HIV-1 envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371): 1884-1888). HIV-1 gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbiol 6(2):143-155). The surface-exposed HIV-1 Env trimer is the sole target for antibodies capable of neutralizing the virus (Burton D R, et al. (2004) Nat Immunol 5(3):233-236). Recently, a myriad of Env-directed broadly neutralizing antibodies (bNAbs) were isolated from numerous HIV-1-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-1 envelope spike. Cell reports 7(3):785-795; Klein F, et al. (2012) J Exp Med 209(8):1469-1479). Infection of macaques by a chimeric model virus, SHIV, can be prevented by prior passive immunization of all bNAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci USA 109(46):18921-18925; Barouch D H, et al. (2013) Therapeutic efficacy of potent neutralizing HIV-1-specific monoclonal antibodies in SHIV-infected rhesus monkeys. Nature 503 (7475):224-228).

Along with virus-specific T cells, an efficacious HIV-1 vaccine therefore would likely need to generate bNAbs targeting Env. Although the premise is simple, in actuality, it is a tremendous challenge without precedent in the history of vaccinology. The difficulty to vaccinate against HIV arises from the extensive variability of Env present on the large number of HIV-1 isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci USA 108(27):11181-11186; Sundling C, et al. (2012) Science translational medicine 4(142):142ra196; Tran K, et al. (2014) Vaccine-elicited primate antibodies use a distinct approach to the HIV-1 primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to V1V2 regions of multiple HIV-1 subtypes correlate with decreased risk of HIV-1 infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-1 infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or E M analysis (Tran K, et al. (2014) Proc Natl Acad Sci USA 111(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-1 primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci USA 109(30):12111-12116; Nkolola J P, et al. (2014) Comparison of multiple adjuvants on the stability and immunogenicity of a clade C HIV-1 gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bNAbs, (GE148 and GE136) generated following immunization of uncleaved gp140 trimers (YU2 gp140-foldon) in non-human primates (NHP). Non-bNAbs, represented by GE136 and 148, can only neutralize the sensitive so-called "tier 1 viruses" that are not representative of the more neutralization resistant tier 2-like primary isolates circulating in the human population. Using crystallography, EM reconstructions, paratope scanning and molecular modeling Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-1 spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer E M reconstruction of KNH1144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNH1144 SOSIP trimers are derived from the Env sequences of the subtype A BG505 and KNH1144 strains. These soluble trimers possess an engineered disulfide linkage between the gp120 and gp41 (at residues 501C and 605C, respectively) and an additional mutation in the heptad repeat 1 (HR1) of gp41 (I559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-1 primary strains were attempted over the past decade, the BG505- and KNH1144-derived SOSIP trimers are the two limited examples of SOSIPs that yield homogeneous trimers suitable for high resolution biophysical and structural analysis. The structural explanation for the difficulty to readily transfer the SOSIP design to other HIV-1 strain-derived sequences is not yet fully understood and would be valuable information to broaden the trimer design horizon.

Here, Applicants describe two SOSIP trimer molecules derived from the B subtype strain, JRFL, and the subtype C strain, 16055. Applicants selected these two Envs for the initial results reported in this study as follows. The JRFL SOSIP trimer, truncated at residue 663 (JRFL SOSIP.663) derives from the JRFL HIV-1 strain isolated from the frontal lobe (FL) of an HIV-1-infected individual. This Env is often used because it displays the unusual property that its gp160 Env precursor is efficiently cleaved into the gp120 and gp41 subunits when expressed on the cell surface of 293F HEK cells (Pancera M & Wyatt R (2005) Virology 332(1):145-156). The 16055 SOSIP.663 trimer, also truncated at residue 663, derives from a HIV-1 Indian strain and displays the unusual property that its monomeric gp120 is recognized by the quaternary epitope-preferring bNAbs, PG9 and PG16, which is relatively infrequent amongst most HIV-1 Env sequences (McLellan J S, et al. (2011) Nature 480(7377): 336-343), and is also observed for BG505 gp120 (Julien J P, et al. (2013) Proc Natl Acad Sci USA 110(11):4351-4356; Hoffenberg S, et al. (2013) J Virol 87(10):5372-5383).

Applicants demonstrate that the JRFL and 16055 SOSIP.663 trimers were purified to homogeneity by a novel means of isolation that utilizes non-bNAbs targeting the CD4-binding site (CD4bs) in a negative-selection process that effectively separates well-ordered trimers from a mixture also containing disordered trimers and other oligomeric states of Env. By binding kinetic analysis, Applicants demonstrated that the purified JRFL and 16055 SOSIP.663 trimers were efficiently recognized by bNAbs but were poorly recognized by the non-bNAbs. By negative stain EM, Applicants confirmed that negative selection results in homogeneous, three-fold symmetric JRFL and 16055 SOSIP.663 trimers resembling the native HIV spike and the previously described subtype A SOSIPs. Applicants obtained 3D EM reconstructions of the unliganded and liganded JRFL and 16055 SOSIP.663 trimers and demonstrated that the negatively selected trimers adopt conformational changes upon sCD4 engagement that emulate those of the native HIV spike (Liu J, et al. (2008) Nature 455(7209): 109-113). Differential scanning calorimetry (DSC) and differential scanning fluorimetry (DSF) revealed that the negatively selected JRFL and 16055 SOSIP.663 trimers were stable at temperatures exceeding 55 and 63° C., respectively. Applicants conclude that the negative-selection process resulted in highly homogenous well-ordered JRFL and 16055.663 trimers, expanding the SOSIP family of Env mimetics to HIV-1 subtypes B and C. This advance provides opportunities for HIV Env structural comparisons at high resolution as well as a wider array of ordered trimers for sequential or simultaneous inoculation regimens to evaluate enhanced immunogenicity toward more broadly effective antibody responses.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or specification.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. *J. Virol.* 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

In another embodiment of the present invention, the soluble envelope glycoproteins of the present invention may be crystallized in the combination with PG9 or PG16 or with any other neutralizing antibodies, including those identified by the above methods, to determine the exact molecular surface where the soluble envelope glycoprotein binds with the neutralizing antibody to design HIV-1 immunogens.

Crystals of the invention may be obtained by conventional means as are well-known in the art of protein crystallography, including batch, liquid bridge, dialysis, vapor diffusion and hanging drop methods (see, e.g., Johnson et al., Biochemistry. 1982 Sep. 28; 21(20):4839-43; Brayer & McPherson, J Biol Chem. 1982 Apr. 10; 257(7):3359-61; McPherson & Weickmann, J Biomol Struct Dyn. 1990 April; 7(5):1053-60; and Koszelak et al., J Mol Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody, such as PG9 or PG16, and soluble envelope glycoprotein in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to a neutralizing antibody, such as PG9 or PG16, and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures of a synthetic or mutated neutralizing antibody, such as PG9 or PG16, domains, as well as the structures of co-crystals of such domains with ligands.

The provision of the crystal structure of a neutralizing antibody, such as PG9 or PG16, complexed with a soluble envelope glycoprotein provide the skilled artisan with a detailed insight into the mechanisms of action of a neutralizing antibody, such as PG9 or PG16. This insight provides a means to design compounds that bind to a neutralizing antibody, such as PG9 or PG16, and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody, such as PG9 or PG16, complexed with a soluble envelope glycoprotein allows a novel approach for drug or compound discovery, identification, and design for compounds that bind to a neutralizing antibody, such as PG9 or PG16, and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody, such as PG9 or PG16, complex as defined by the co-ordinates or the identifying co-ordinates, providing a structure of a candidate compound; and fitting the structure of the candidate to the structure of a neutralizing antibody, such as PG9 or PG16.

In an alternative aspect, the method may use the co-ordinates of atoms of interest of a neutralizing antibody, such as PG9 or PG16, which are in the vicinity of the active site or binding region in order to model the pocket in which the substrate or ligand binds. These co-ordinates may be used to define a space which is then screened "in silico" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody, such as PG9 or PG16, as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody, such as PG9 or PG16, which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody, such as PG9 or PG16; and fitting the structure of the candidate to the co-ordinates of the sub-domain provided.

The invention further provides a method for determining the structure of a binder of a neutralizing antibody, such as PG9 or PG16, bound to a neutralizing antibody, such as PG9 or PG16, comprising: providing a crystal of a neutralizing antibody, such as PG9 or PG16, e.g., according to the invention, soaking the crystal with the binder, and determining the structure of the neutralizing antibody-binder complex. Alternatively or additionally the neutralizing antibody, such as PG9 or PG16, and the binder may be co-crystallized.

The invention also provides a method of analyzing a complex of a neutralizing antibody, such as PG9 or PG16, and a potential binder comprising: employing X-ray crystallographic diffraction data from the complex and a three-dimensional structure of a neutralizing antibody, such as PG9 or PG16, or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, such as PG9 or PG16, and the solved structure of an uncomplexed neutralizing antibody, such as PG9 or PG16. These maps can then be used to determine whether and where a particular potential binder binds to a neutralizing antibody, such as PG9 or PG 16, and/or changes the conformation of a neutralizing antibody, such as PG9 or PG16. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Determination of the 3D structure of a neutralizing antibody, such as PG9 or PG16, provides important information about the likely active/binding site(s) of a neutralizing antibody, such as PG9 or PG16. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

In yet another embodiment, the present invention also encompassed the use of the soluble envelope glycoproteins described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

F(ab')$_2$, the fragment of the antibody that can be obtained by treating whole antibody with the enzyme pepsin without subsequent reduction; F(ab')$_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus F with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions are generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

In an advantageous embodiment, the mutation is a proline substitution. Stabilization of the native Env trimer in the "NFL" platform involves and encompases a HR1 destabilization screen with proline substitutions.

The present invention also encompasses the I559P change in the BG505 NFL trimers.

The present invention also involves stabilizing the clade C 16055 Env trimers in their native-like conformation in the NFL platform and to find out a common proline mutation that can be easily translated to stabilize majority of the ENV trimers spanning different clades.

In the native spike, the gp41 subunit exists in a metastable conformation and it favorably forms a stable post-fusion six-helix bundle (6HB), which is composed of trimers of HR1 (N-heptad repeat) and HR2 C-heptad repeat) heterodimers facilitating the fusion of HIV with the host CD4 T cells. The formation the 6HB is a irreversible process destabilizing the native trimer resulting in exposure of immunodominant and non-neutralizing epitopes to the immune system. Ideally, any mutation in the HR1 or HR2 that can destabilize the 6HB formation will stabilize the Env trimers in a native-like conformation.

In an initial screen 30 residues from HR1 and 3 residues from HR2 were selected. The HR1 residues were mutated individually to proline. The HR2 residues were mutated to proline and other charged residues (Aspartic acid, Glutamic acid and Arginines). Five single proline mutants (L555P, Q652P, Q653P, L565P and L566P) stabilize the clade C 16055-NFL2 Env trimers in the native-like conformations. Five double mutants stabilize and induce native-like trimer formation in 16055-NFL2 Env.

Figure 6:
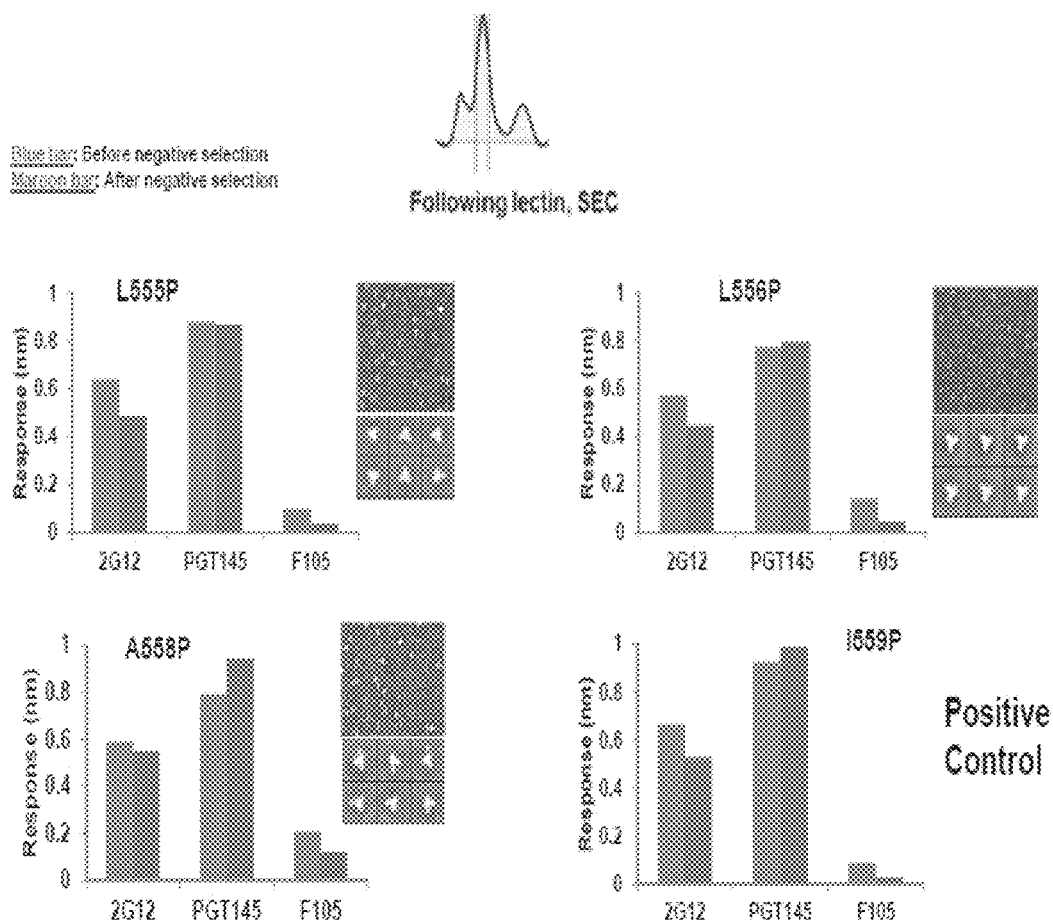
FIG. 6 depicts octet binding data and EM that suggest L555P, L556P, and A558P are other prolines similar to I559P.
Figure 7A:
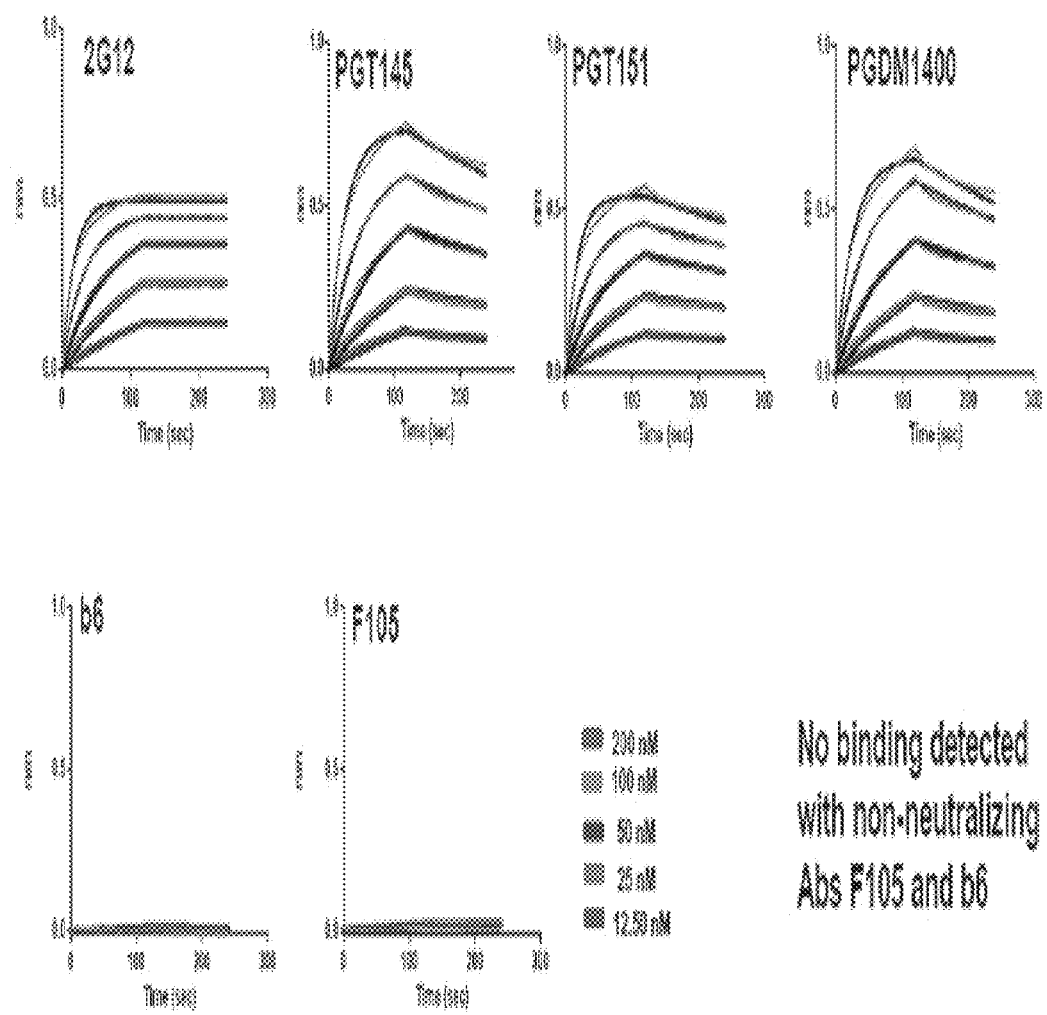
Figure 8:
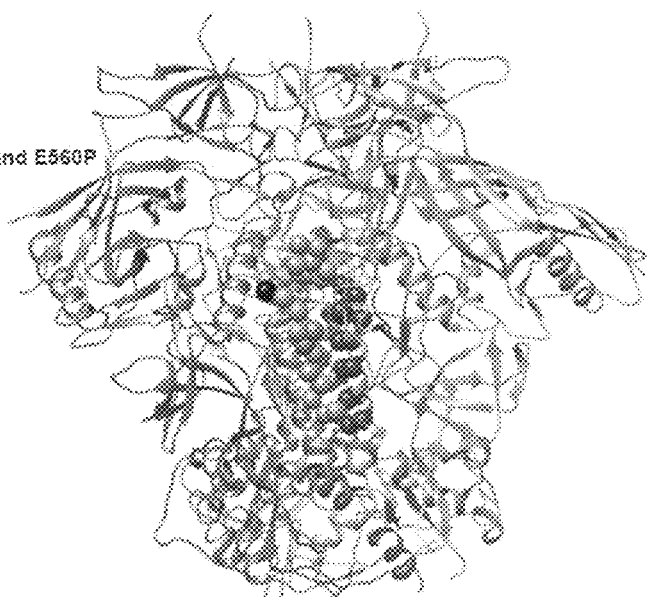
FIG. 8 depicts a screening summary of BG505/16055 NFL.
Figure 9:
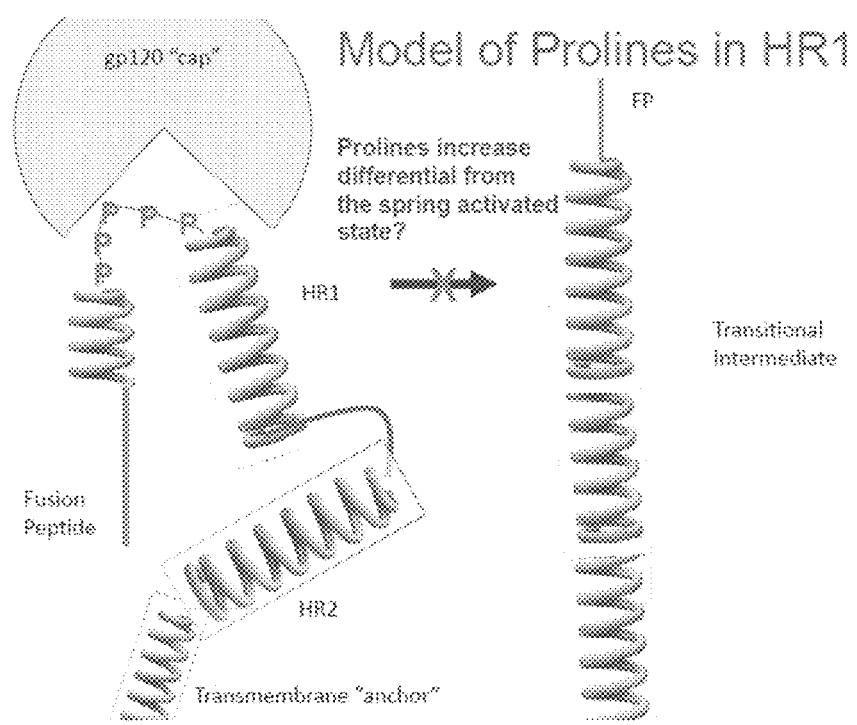
FIG. 9 depicts a model of prolines in HR1.
Figure 12:
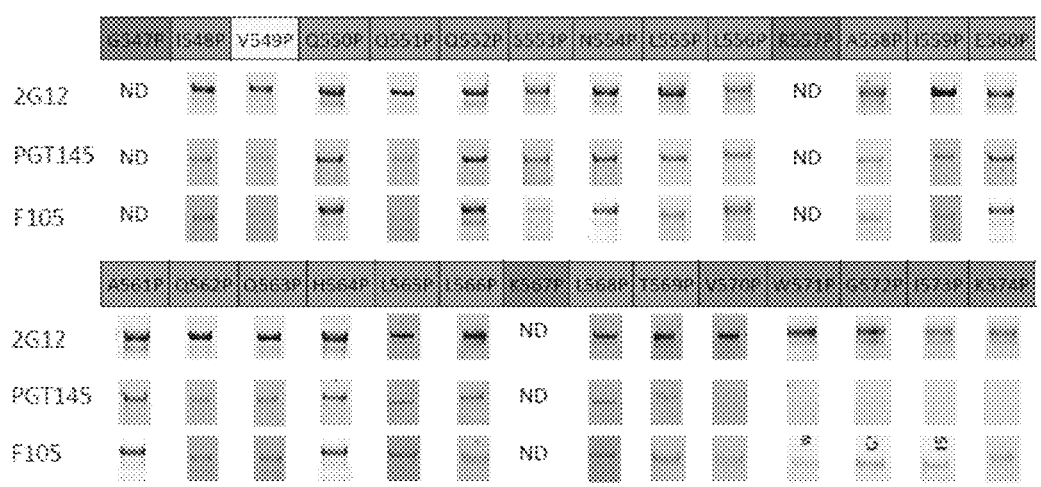
FIG. 12 depicts BG505-NFL2 IP results.
Figure 13:
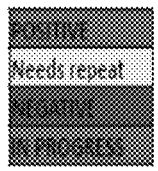
FIG. 13 depicts BG404-NFL2 IP results and 16055-NFL2 IP results.
Figure 14:
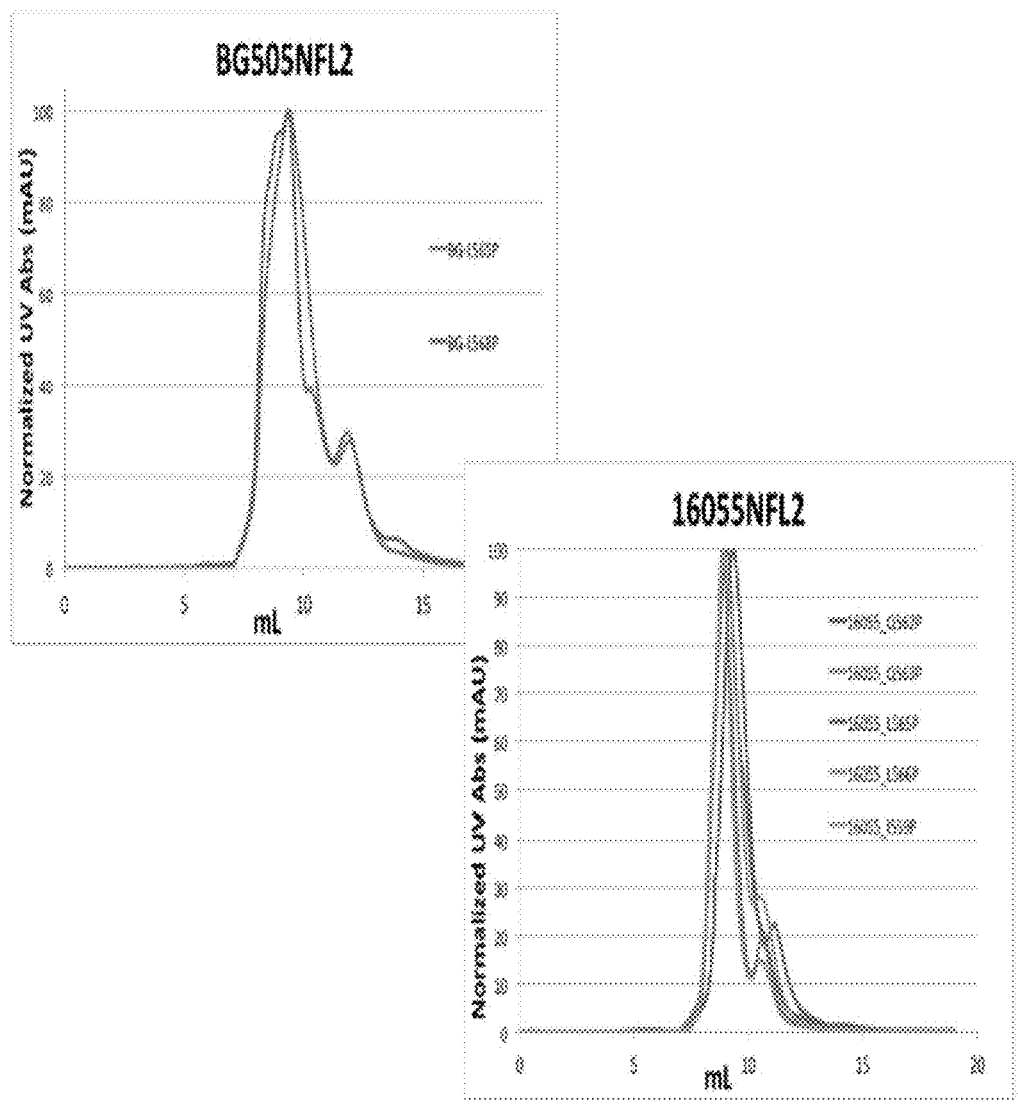
FIG. 14 depicts SEC profiles.
Figure 15A:
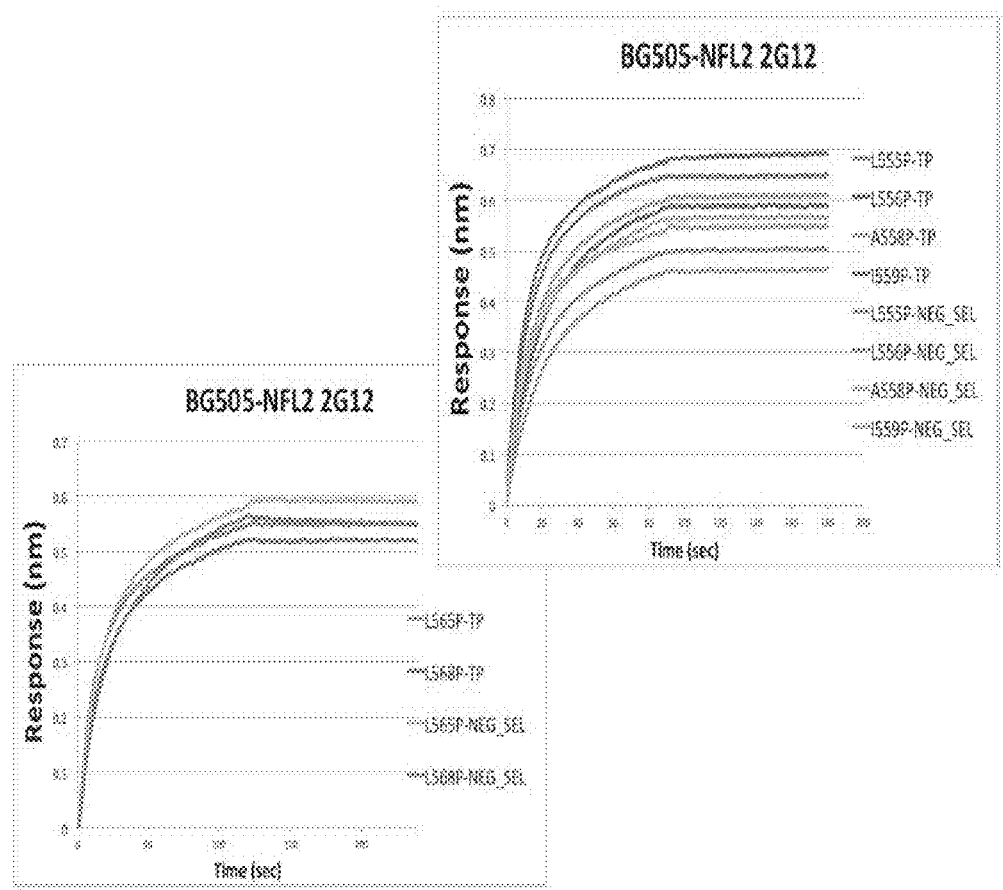
FIGS. 15A-C depicts BG505-NFL2 octet results.
Figure 15B:
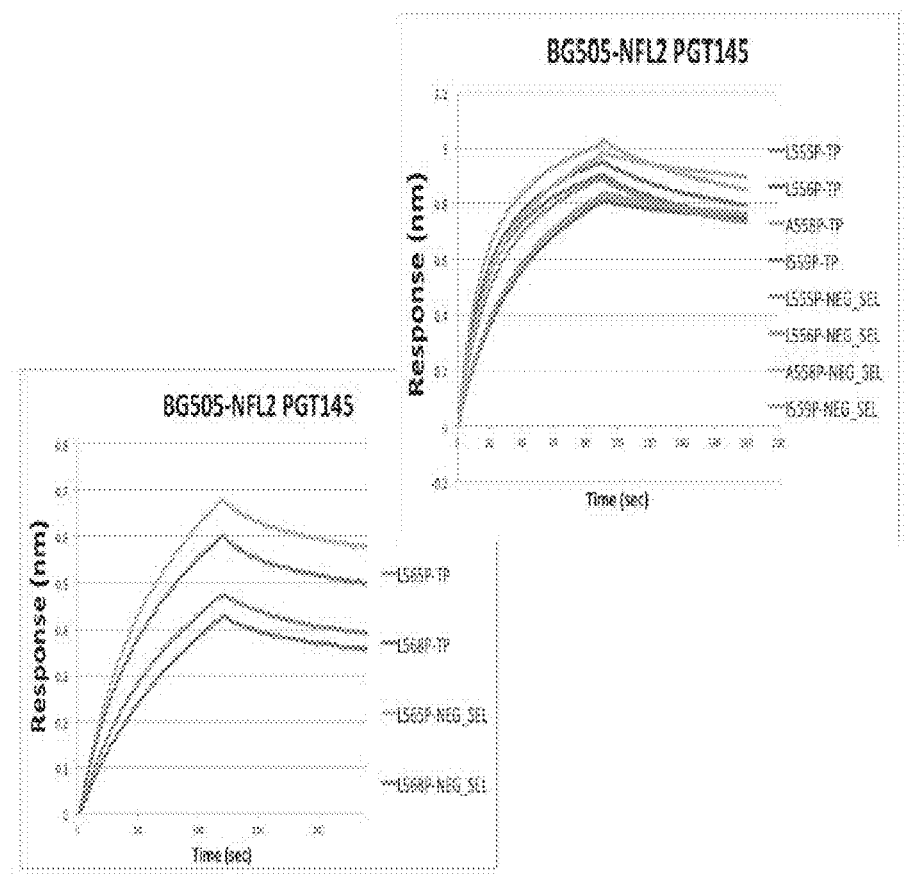
Figure 15C:
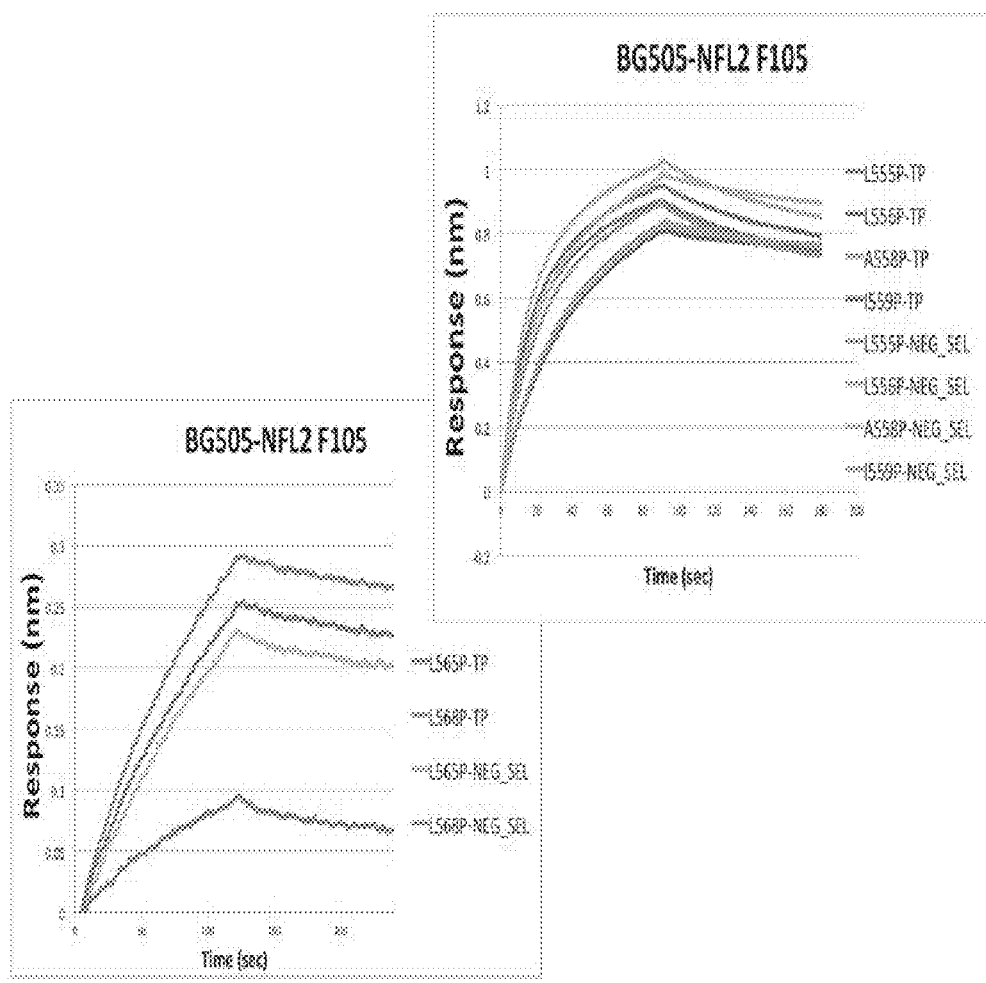
Figure 17A:
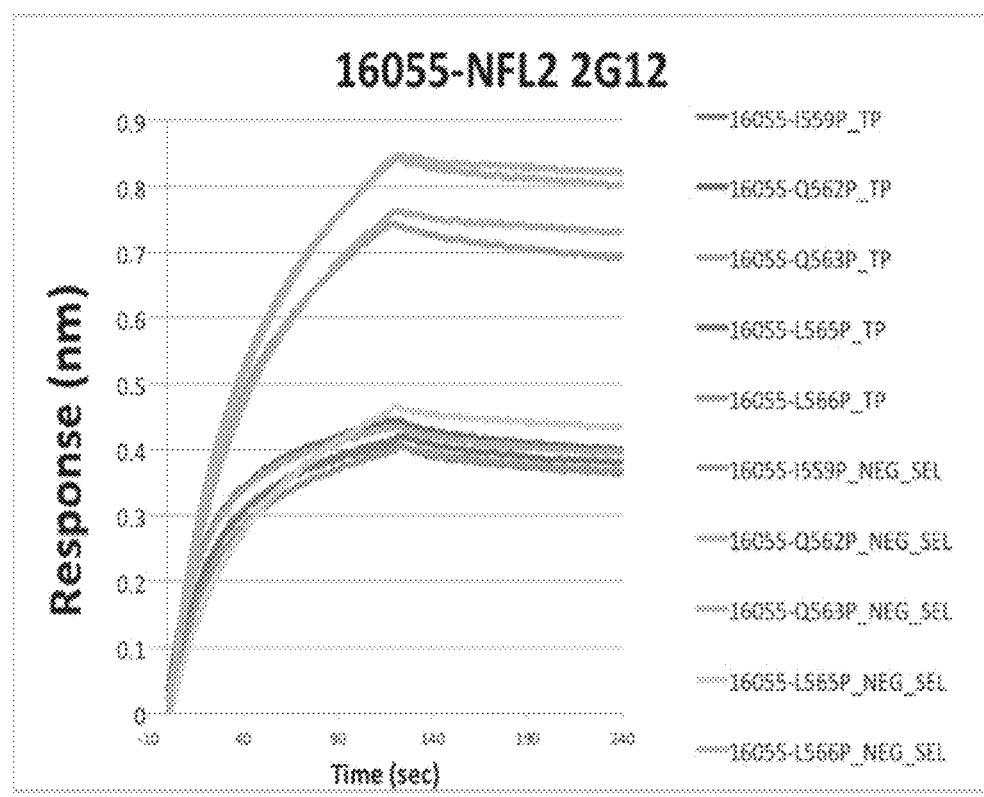
FIGS. 17A-C depict 16055-NFL2 octet results.
Figure 17B:
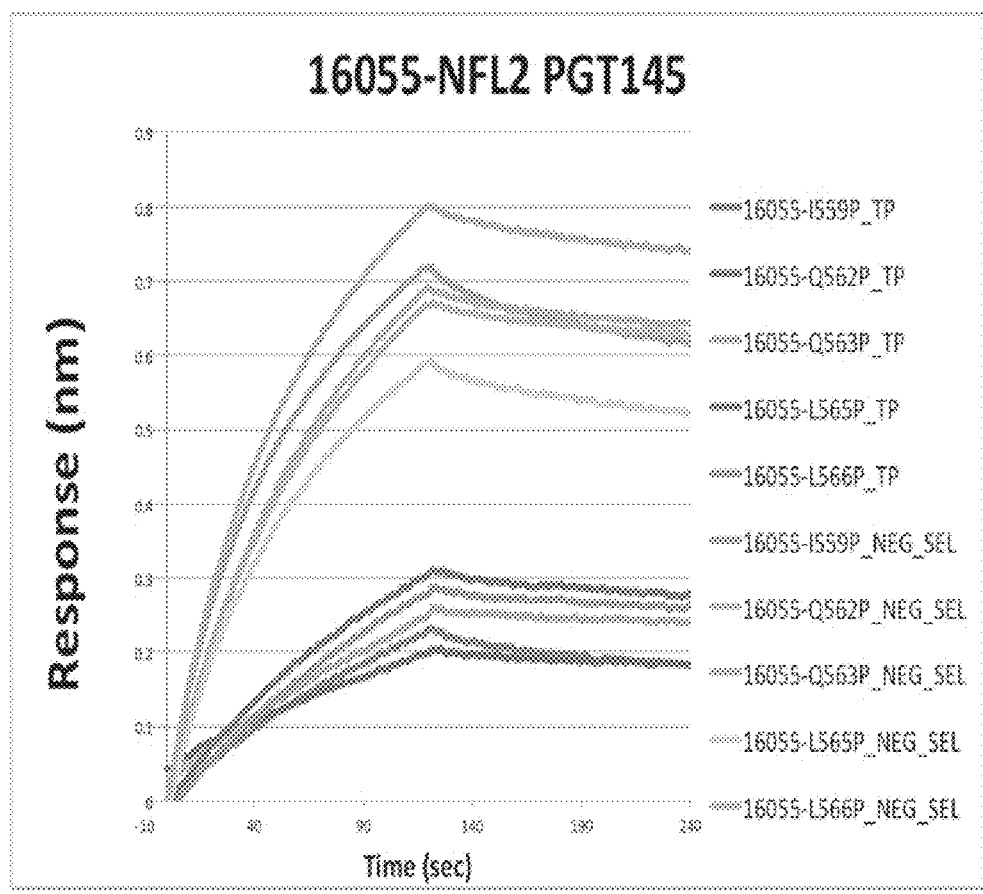
Figure 17C:
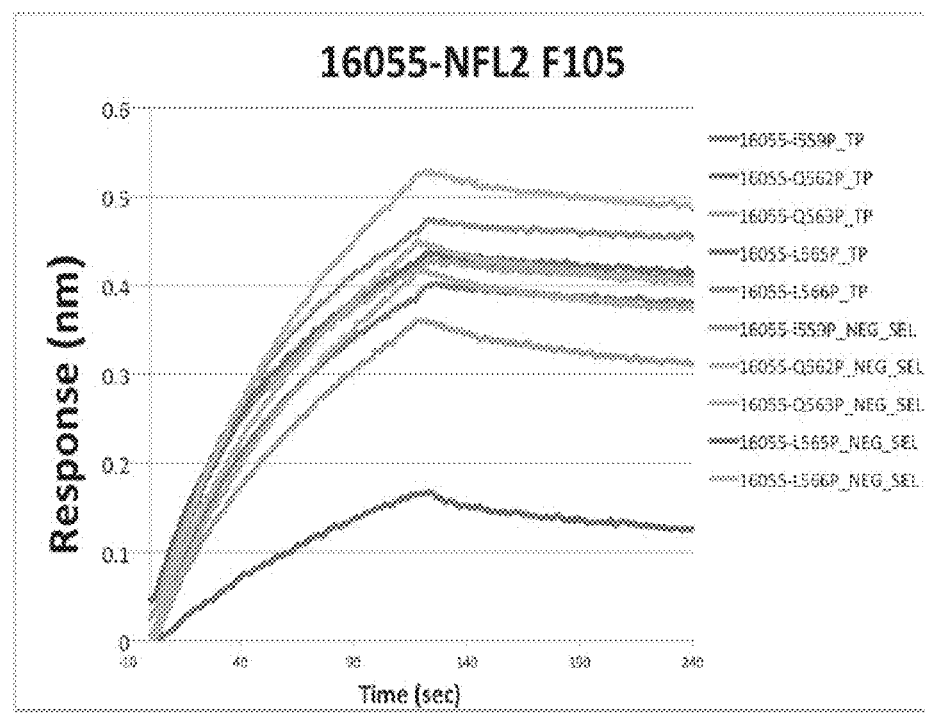
Figure 19:
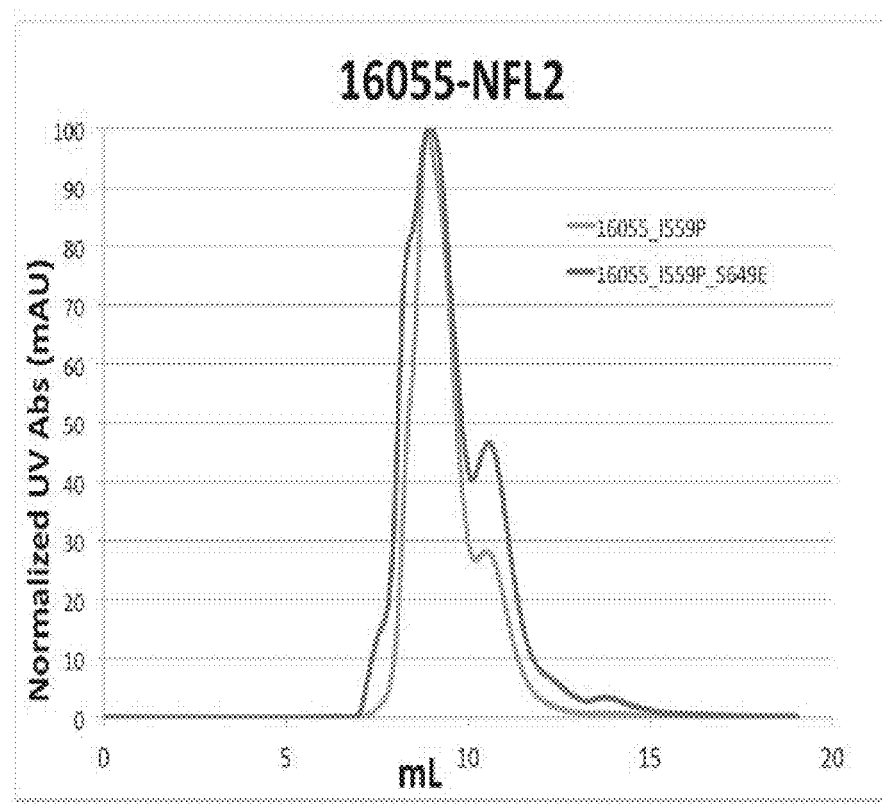
FIG. 19 depicts a HR2 double mutant SEC profile.
Figure 20:
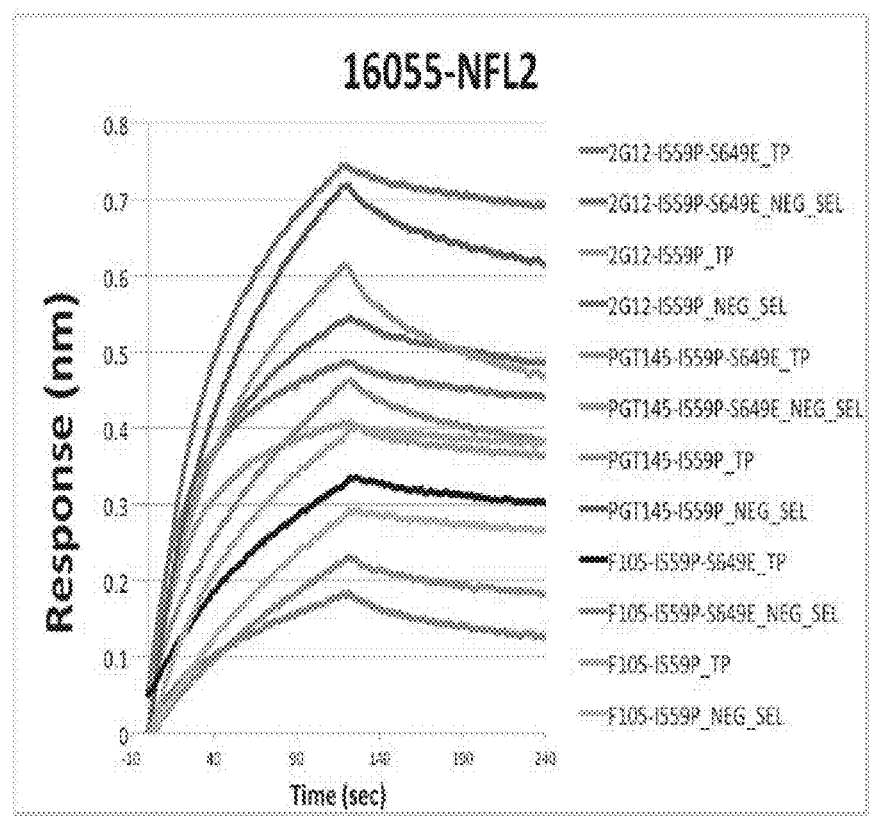
FIG. 20 depicts HR2 double mutant OCTET results.

The present invention encompasses mutations of 36 residues from HR1 that are individually mutated to proline (see, e.g., FIGS. 4A and 4B) in a BG505-NFL2 trimer. Octet binding data and EM suggest L555P, L556P, and A558P are other prolines similar to I559P (see, e.g., FIG. 6). In particular, L555P was recognized efficiently by bNAbs and trimer-preferring bNAbs (see, e.g., FIG. 7). In an advantageous embodiment, preferred mutations include, but are not limited to, S553P, N554P, L555P, E560P, Q562P, Q563P or any combination thereof.

The present invention encompasses mutations of residues from HR1 that stabilize a clade C 16055-NFL2 trimer. (see, e.g., FIG. 16). In an advantageous embodiment, preferred mutations include, but are not limited to, L555P, Q652P, Q653P, L565P, L566P or any combination thereof.

The present invention encompasses mutations of residues from HR1 that stabilize a JRFL-NFL2 trimer. (see, e.g., FIG. 21). In an advantageous embodiment, preferred mutations include, but are not limited to, L555P, N554P, I559P, Q562P, Q563P, S649D or any combination thereof.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823;

5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (DEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)$ $_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

High-Density Array of Well-Ordered HIV-1 Spikes on Synthetic Liposomal Nanoparticles Efficiently Activate B Cells A major step towards an HIV-1 vaccine is an immunogen capable of inducing neutralizing antibodies. Envelope glycoprotein (Env). mimetics, such as the NFL and SOSIP designs, generate native-like, well-ordered trimers and elicit tier 2 homologous neutralization (SOSIPs). Applicants reasoned that the display of well-ordered trimers by high-density, particulate array would increase B cell activation compared to soluble trimers. Here, Applicants present the design of liposomal nanoparticles displaying well-ordered Env spike trimers on their surface. Biophysical analysis, cryo- and negative-stain electron microscopy and binding analysis with a panel of broadly neutralizing antibodies confirm high-density, well-ordered trimer particulate array. The Env trimer-conjugated liposomes were superior to soluble trimers in activating B cells ex vivo and germinal center B cells in vivo. In addition, the trimer-conjugated liposomes elicited modest tier 2 homologous neutralizing antibodies. The trimer-conjugated liposomes represent a promising initial lead towards the development of more effective HIV vaccine immunogens.

A broadly effective HIV-1 vaccine will likely require the elicitation of broadly effective neutralizing antibodies. Although broadly neutralizing antibodies (bNAbs) arise sporadically following chronic HIV infection such bNAbs are exceedingly difficult to elicit by vaccination(Burton et al., 2004). One roadblock to the elicitation of neutralizing antibodies by vaccination has been the development of an immunogen that stably presents a gp120-gp41 envelope glycoprotein (Env) trimer in its native state, as it is presented on the virus surface. With the recent developments of SOSIP and NFL trimeric Env platforms, it is now possible to express and purify soluble, native-like and well-ordered Env trimers that are structurally and antigenically well characterized (Guenaga et al., 2015; Julien et al., 2013; Pancera et al., 2014; Sharma et al., 2015). To date, these trimeric mimetics of the HIV-1 native spike elicit homologous "tier 2" neutralization to a few selected strains of undetermined long-term durability (Sanders et al., 2015) and most potently in small animals. Although this is a promising first step, the next step is to quantitatively or qualitatively increase B cell activation elicited by the well-ordered trimers, toward the longer-term goals of increased somatic hypermutation and more durable antibody responses leading to trimer-dependent elicitation of broader neutralizing activity.

An impediment to elicit neutralizing antibodies by HIV itself or HIV-based virus-like particles (VLP) may be the low levels of natural Env incorporation, resulting in sparse numbers of spikes per VLP (Deml et al., 1997). Here, Applicants generated Ni+2-bearing, fully synthetic single bilayer liposomes arrayed with the newly developed, well-ordered HIV-1 soluble trimer mimetics possessing three C-terminal His-tags per trimer. This design allows the variable incorporation of Ni+2-lipids to generate a series of JRFL trimer-conjugated liposomes displaying different levels of either SOSIP or NFL well-ordered (Kovacs et al., 2014; Sanders et al., 2013; Sharma et al., 2015) trimers arrayed on the liposomal surface. This means of high-density particulate display as well blocks access to the non-neutralizing, non-glycosylated underside of the trimers. This solvent accessible surface, usually occluded by the viral lipid bilayer, was recently shown to be highly immunogenic using soluble BG505 SOSIP trimers (Hu et al., 2015) in mice, however no "tier 2" autologous neutralizing antibodies were detected as they are in rabbits (Sanders et al., 2015). HIV gp140 trimers conjugated to interbilayer-cross-linked multilamellar vesicles (ICMVs) generate high titer binding responses in mice (Pejawar-Gaddy et al., 2014) and biotin-labeled gp120 onto avidin-containing liposomes stimulate anti-gp120 B cells in vitro (Ota et al., 2013), however well-ordered Env trimers arrayed at high-density particulate array have not been assessed in an animal model capable of generating tier 2 autologous neutralization.

In the current study, Applicants showed by biochemical and biophysical analysis, cryo-electron microscopy (EM) and negative staining-EM that the predominantly single bilayer liposomes, when optimized, present the well-ordered trimers with high-density, multi-valent array. On the liposome surface, these well-ordered trimers retained qualities of a closed native trimer and were stable for several months at 4° C. Applicants demonstrated that this high-density array better activated B cells ex vivo compared to strain-matched soluble trimers and that the liposome-conjugated trimers more efficiently generated germinal center B cells compared to soluble trimers in a statistically significant manner. Compared to the soluble trimers, there was a trend for the liposome-conjugated trimers to more efficiently elicit binding antibodies to native-like trimers and modest tier 2 (JRFL) homologous neutralizing titers. The clinical efficacy of human papillomavirus (HPV) L1 virus-like particles (VLPs) to provide long-lasting protection against a virus that enters by mucosal routes, while, in contrast, the HPV L1 monomer is not protective suggests that particulate display of ordered HIV trimers might hasten development toward a more effective HIV-1 vaccine (Caldeira Jdo et al., 2010; Safaeian et al., 2013), (Schiller and Chackerian, 2014; Schiller and Lowy, 2015). Combining the well-ordered trimers with particulate high-density display presents a scalable platform to enhance B cell responses to HIV-1 Env and potentially to envelope glycoproteins from other viruses that are relevant vaccine targets.

Figure 22B:
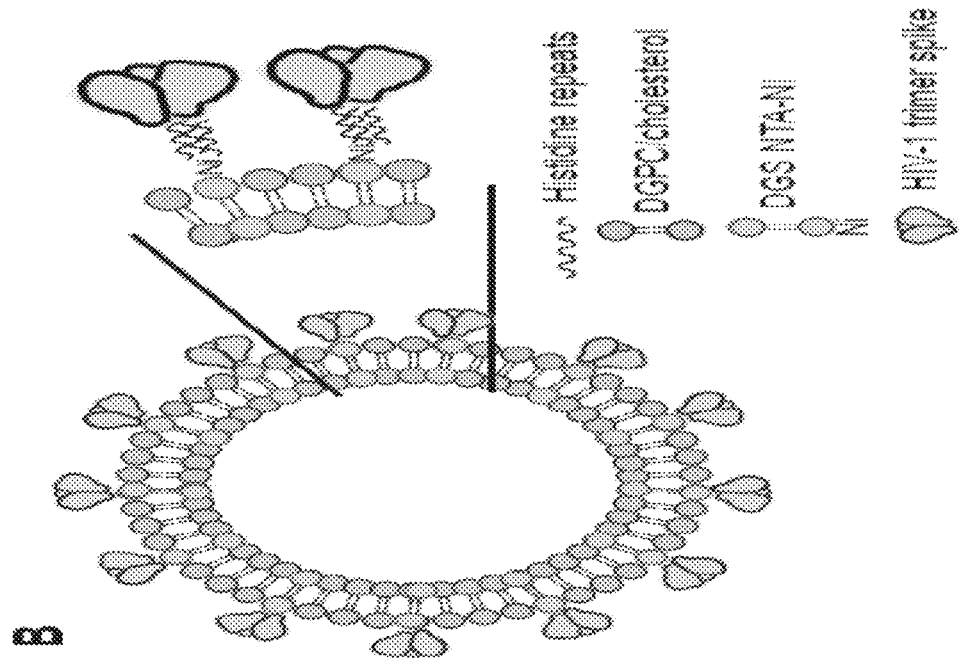
FIGS. 22A-B depict HIV trimers and their particulate display. (A) Negative stain EM micrographs of JRFL gp140-foldon oligomers, JRFL NFL2P, and JRFL SOSIP trimers. Scale bars=20 nm. (B) Schematic representation of liposomes displaying HIV-1 trimers. Zoomed field depicts binding of the 6-histidine repeats (His6 tag) present as a fusion on the C-terminus of each protomer of each trimer to the Ni+2 chelated at the hydrophilic head group of the DGS-NTA(Ni) polar lipid.
Figure 22A:
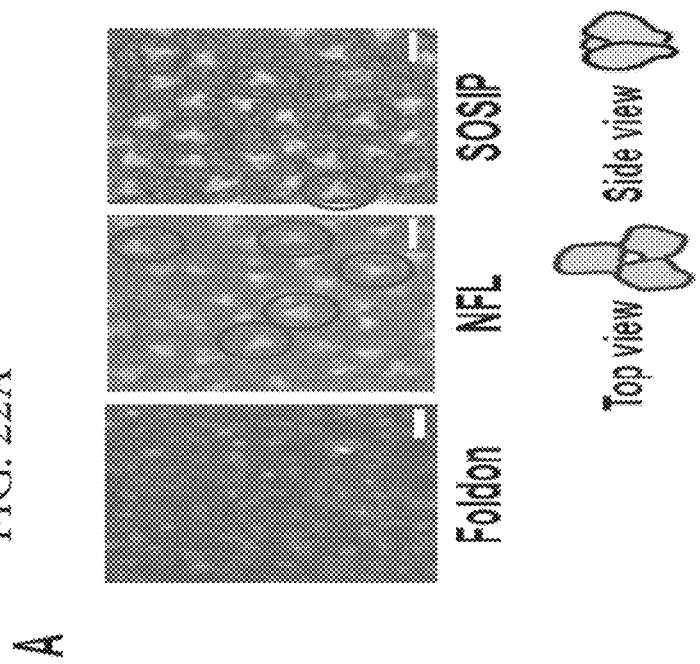

Well-ordered His-tagged trimers for liposomal array. The development of well-ordered trimers by two independent platforms, SOSIP and NFL, present the opportunity to assess the multivalent array of such trimers on the surface of liposomal nanoparticles to study their impact on antigenicity and immunogenicity. These well-ordered trimers are well characterized by negative stain followed by EM at both the level of 2D classifications and 3D reconstructions, including the JRFL strain-derived trimer prototypes used here (Guenaga et al., 2015; Sharma et al., 2015). To contrast the ordered appearance of the JRFL SOSIP and NFL trimers with the previously described disordered foldon trimers (Ringe et al., 2015; Tran et al., 2014) Applicants performed negative staining followed by EM at the level of resolution amenable for analysis of liposomes. As shown in FIG. 22A (left panel), the previously described JRFL-based gp140-foldons displayed an amorphous mixture of oligomeric states. In contrast, the more faithful mimetics of the HIV-1 Env spike, JRFL SOSIP and NFL trimers, presented a relatively well-ordered appearance. Depending upon the random orientation of the trimers on the carbon-coated grid, the soluble spikes displayed 3-fold symmetry typified by a "propeller-like" appearance by negative staining-EM, at the level of resolution analyzed here (FIG. 22A, center and right panels). With the well-ordered trimers in hand, each containing C-terminal His6-tags on each protomeric subunit, Applicants sought to array these spike mimetics on a repetitive, nanoparticle platform to assess potential improvements in B cell activation and immunogenicity. Applicants generated liposomes by standard procedures comprised of a mixture of 60% 1,2-distearoyl-sn-glycero-3-phosphocholine (DGPC) and 40% cholesterol (Avanti Polar Lipids). Applicants used a relatively high concentration of cholesterol to increase liposomal membrane stability and integrity in vivo (Arsov and Quaroni, 2007). In brief, polar lipids in chloroform were dried onto glass, re-suspended in aqueous buffer, sonicated in the buffer and extruded through filters to generate approximately 100 nm diameter nanoparticles. To produce His-binding liposomes, Applicants incorporated 1,2-dioleoyl-sn-glycero-3-((N-(5-amino-1-carboxypentyl) iminodiacetic acid)succinyl) (nickel salt) (DGS-NTA-Ni) into the lipid mixture at levels of 1 to 4%, substituting for the cholesterol lipid component. Applicants reasoned that the NTA-Ni would randomly disperse in the lipid bilayer, and that approximately 50% of the time, the polar head groups would align on the outside of the lipid bilayer to be available for conjugation with the His-tags present on the C-terminus of the ordered HIV-1 trimers (see schematic, FIG. 22B). Applicants could also incorporate TLR ligands into the liposomes by including them in the chloroform mixture prior to drying the lipids on to the glass surface.

Analysis of well-ordered trimers coupled to liposomes by SDS-PAGE and EM. Following incubation of the well-ordered NFL and SOSIP His-tagged timers with the Ni-bearing liposomes, containing 1, 2 and 4% DGS-NTA(-Ni) lipids, respectively, Applicants performed size exclusion chromatography (SEC) to separate free trimers from liposomes. Next, Applicants analyzed the liposomes by SDS-PAGE and detected increasing trimer bands with increasing levels of Ni+2 incorporated into the liposomes following staining of the gel by Commassie blue solution (FIG. 23).

Figures 29A, 29B:
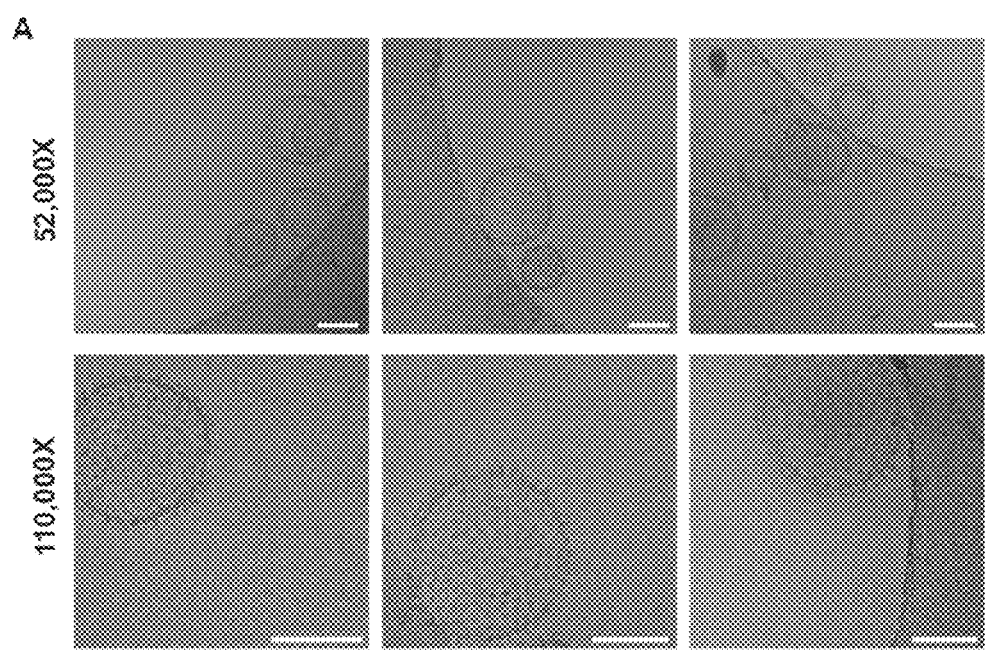
FIGS. 29A-B depict characterization of JRFL NFL-conjugated liposomes. (A) Cryo-electron microscope images of 4% Ni JRFL NFL-conjugated liposomes at 52,000 and 110,000× magnification. Scale bar=100 nm. (B) Cryo-electron microscope image measuring the diameter of the JRFL NFL-conjugated liposomes.

Applicants subjected the 4% DGS-NTA(Ni) liposomes to dynamic light scattering (DLS) to assess liposomal diameter and uniformity before and after conjugation with the well-ordered NFL or SOSIP trimers. As shown in FIG. 23B, the non-conjugated liposomes displayed an average diameter of 152 nm while the average diameter of trimer-conjugated liposome was 172 nm. To further assess liposome uniformity, diameters and to visually determine state of trimers arrayed on the surface of the liposomes, Applicants performed cryo-EM of both the JRFL SOSIP- and JRFL NFL-conjugated 4% DGS-NTA(Ni) liposomes (FIG. 23 and FIG. 29A). Using the cryo-EM images, Applicants measured the liposome diameters to be from 75 nm to 250 nm (see FIG. 29B), consistent with the DLS data. Using the measuring tools, Applicants determined the lipid bilayer to be ~5 nm in width with individual trimers spaced at ~12-14 nm apart on the liposomes. As detected by the cryo-EM analysis, the majority of liposomes possessed a single lipid bilayer and virtually all nanoparticles displayed a high-density array of the SOSIP or NFL trimers, respectively. An apparent double lipid bilayer was visible on a small percentage of liposomes and, for even fewer, multiple layered lipid bilayers were observed (FIG. 29A), all possessing trimers on their outermost surface. The liposome interior appeared to contain only buffer as no other density was observed in the enclosed volumes. In addition, no other materials were observed in the sample, indicating that the sample was free of any adventitious agents.

To increase contrast and resolution of the trimers arrayed on the liposomal surface, Applicants performed negative staining followed by EM at selected magnifications of the trimer-conjugated liposomes. As seen in FIG. 24, with 1% Ni-lipid formulation, the conjugated well-ordered trimers were detected as a "ring" visible around the circumference of the liposomes, observable by EM in what appeared to be two dimensions. In the case of the 2% Ni-containing liposomes, beside trimers ringing the circumference of individual nanoparticles, trimers could be detected on the surface of the liposomes encircled by the lipid bilayer. For the 4% Ni-containing liposomes, Applicants observed densely packed and evenly spaced trimers arrayed on the surface of the liposomes by the negative staining-EM. The patterns of trimer array were very similar for both the JRFL SOSIP- and JRFL NFL Env-containing liposomes. Because the trimers were relatively well resolved, Applicants next quantitated the approximate number of trimers per liposomal field by constructing a grid to aid manual counting (see FIG. 24B). The total number of trimers per visible field was in the range of 300 spikes per liposome, likely an underestimate since not all surfaces of the liposome are observable in these EM images. Using iTEM (EMSIS, GMbH) measuring tools, Applicants determined the relatively uniformly arrayed trimers to be spaced approximately 14-15 nm apart, center-to-center, on the surface of the nanoparticles (see FIG. 24C and FIG. 24D). In addition, Applicants constructed a square area of approximately 12 nm per side that would encompass each trimer, and adjacent unoccupied surface area, to circumscribe an area of ~144 nm2. Applicants calculated the surface area of a spherical liposome with a radius of ~75 nm to be 70,865 nm2 and by simple division would yield ~492 trimers per liposome, bracketing an estimated range between 300 and 500 trimers per particle.

To confirm that trimer conjugation to the liposomes was Ni-dependent, DGPC liposomes without any Ni-lipid were generated and the JRFL SOSIP trimers were added to assess interaction. Most trimeric glycoprotein remained dissociated from the liposomal fraction by SEC and EM further confirmed that no trimers were associated with the Ni-lacking liposomes (FIG. 30A).

Binding analysis of the liposome bound trimers by biolayer light interferometry (BLI) and EM. Applicants next assessed if the well-ordered trimers maintained quaternary packing on the surface of the liposomes by probing the trimers with selected bNAbs and mAbs using BLI. Accordingly, Applicants captured the trimer-conjugated liposomes on the Octet sensor surface by wheat germ agglutinin (WGA), which recognizes and binds to carbohydrates that are abundant as N-glycans located on the trimeric spike surface. In this format, due to the dense array of the trimers on the liposomal surface, there will be avidity effects in regards to the bivalent IgGs as analytes, therefore Applicants used the BLI binding analysis not to derive actual affinities, but to qualitatively assess relative avidities to confirm that once the trimers were conjugated to the liposomes, they displayed the same binding pattern as assessed previously by more quantitative binding kinetics (Guenaga et al., 2015; Sharma et al., 2015). Using the WGA capture of the trimer-conjugated lipoosomes, Applicants did attempt binding by selected Fabs to obtain affinities, but due to the smaller mass of the Fab relative to the liposomes, Applicants could not detect reliable signals by this approach, so Applicants proceeded with the qualitative binding assessments using bivalent IgG.

Figure 25A:
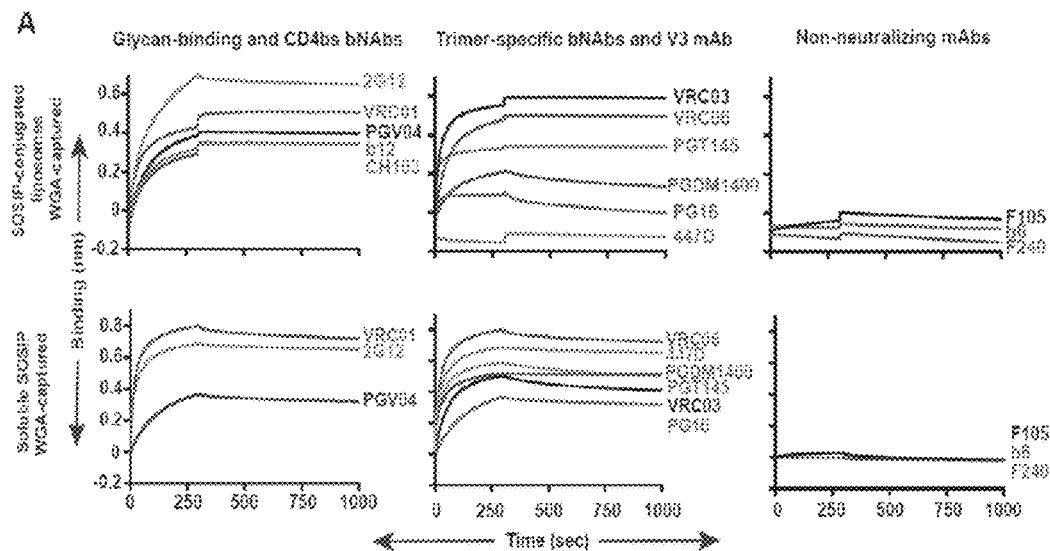
FIGS. 25A-B depict binding of HIV-1 antibodies to JRFL SOSIP trimer-conjugated liposomes and soluble JRFL SOSIP trimer assessed by Bio-Layer Interferometry using Octet and negative stain EM. (A) JRFL SOSIP trimer conjugated to 4% DGS-NTA(Ni) liposomes (equivalent to 75 nmoles of phospholipids) or JRFL SOSIP trimers (10 mg/ml) were immobilized on WGA-captured streptavidin sensors and 20 mg/ml monoclonal antibodies (IgGs) were used as analyte. (B) 2% DGS-NTA(Ni) liposomes conjugated to JRFL SOSIP were incubated with 10 molar excess of respective IgG mAbs at 37° C. for 30 min, stained with phospho-tungstate, viewed by EM and images were obtained with a CCD camera. All images are at 180,000× magnification. Scale bar=100 nm. See also FIG. 31.

To begin the avidity analysis, Applicants assessed recognition by the CD4 binding site-directed bNAb, VRC01(Wu et al., 2011) and the glycan-dependent 2G12, to determine overall levels of liposome-conjugated trimers, since these mAbs can recognize trimeric or monomeric forms of HIV Env (FIG. 25A). The VRC01 and 2G12 bNAbs efficiently recognized the trimers conjugated to the liposomes, consistent with previous binding studies, and the EM analysis presented here, as did the other CD4bs-directed bNAbs PGV04 (Falkowska et al., 2014), CH103 (Liao et al., 2013) and b12 (Burton et al., 1994). Applicants then utilized the trimer-specific, V2-directed bNAb, PGT145 (McLellan et al., 2011), to confirm that, following conjugation, the quaternary variable region cap of the trimers remained intact. As expected, the trimer-specific PGT145 bNAb efficiently recognized the trimers arrayed on the liposomal surface as did other trimer-preferring bNAbs such as VRC03 (Li et al., 2012; Tran et al., 2012), VRC06 (Li et al., 2012), PGDM1400 (Sok et al., 2014) and PG16 (Pejchal et al., 2010) (FIG. 25A). In contrast, the V3 loop specific mAb, 447-52D (Stanfield et al., 2004), did not bind to the JRFL NFL or JRFL SOSIP trimers on the liposomes, indicating that the V3 region of these trimers is not accessible when arrayed on the liposomal surface. These results contrast with the BLI binding data shown here (FIG. 31A), and previously published data (Sharma et al., 2015) that were generated with the JRFL ordered trimers in solution and 447-52D on the sensor surface. In this configuration, the well-ordered JRFL trimers were well recognized by the V3-directed mAb. To confirm this result in the same binding format used for the liposomes, Applicants assessed 447-52D recognition of the JRFL SOSIP and JRFL NFL trimers when they were captured on the WGA sensors. In this context, 447-52D recognized the trimers, indicating occlusion of the V3 region occurs only when the trimers are arrayed on the liposomal surface. The non-neutralizing mAb, F105 (Posner et al., 1993), does not efficiently recognize the soluble JRFL NFL or SOSIP trimers (Guenaga et al., 2015; Sharma et al., 2015) (FIG. 25A and FIG. 31B), but does efficiently recognize disordered trimers, such as foldon (Guenaga et al., 2015;

Sharma et al., 2015). Here, F105 did not recognize the liposome-conjugated trimers as assessed by BLI, indicating the maintenance of a well-ordered trimeric state following liposomal conjugation (FIG. 25A and FIG. 31C). Since the previous affinities using selected bNAbs were not determined by WGA capture but by His-tag capture of the JRFL trimers (Guenaga et al., 2015; Sharma et al., 2015), Applicants performed a comparative binding analysis with most of the antibodies used to probe the trimer-conjugated liposomes to confirm the relative rank order of the antibody avidities to the trimers and the apparent occlusion of V3 on the trimer-conjugated liposomes (FIG. 25A).

Figure 25B:
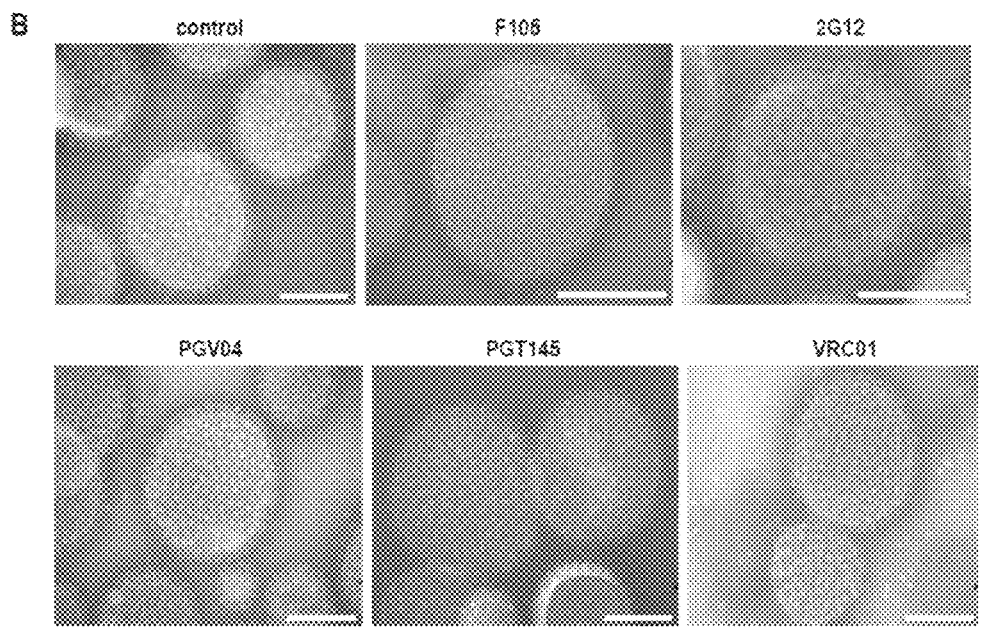

Applicants then probed both JRFL SOSIP and NFL trimers arrayed on the 2% DGS-NTA(Ni)-lipid-containing liposomes with a subset of Env-directed antibodies, but now qualitatively analyzed by negative stain EM, to determine relative accessibility of the neutralizing and non-neutralizing epitopes once the trimers are coupled to the solid phase. Consistent with the binding analysis, when the Env trimer-conjugated liposomes were incubated with non-neutralizing F 105 mAb, in excess, there was no detectable binding to the ordered trimers compared to the unliganded control trimer-conjugated liposomes (FIG. 25B and FIG. 31D). In stark contrast, when the glycan-directed bNAb, 2G12 (Trkola et al., 1996) was incubated with the trimer-conjugated liposomes, the propeller-like pattern of the well-ordered trimers was noticeably perturbed by this full IgG. Similarly, but with less disruption of trimer symmetry, PGV04 and PGT145 binding to the trimers could be observed following incubation and negative stain EM (FIG. 25B and FIG. 31D).

Stability of trimer-conjugated liposomes at selected temperatures by EM. Applicants next sought to determine the stability of the trimer-conjugated liposomes in aqueous buffer at both 4° C. and 37° C. Accordingly, Applicants stored the liposomes at 4° C. for an extended period of time and assessed overall conformation by negative stain EM. Both the liposomes and the trimers arrayed on the surface of these nanoparticles were very stable for up to 4 months at 4° C. (FIG. 30B). Applicants performed the same analysis of trimer-bound liposomes stored at 37° C. and detected more of an impact on both the liposomes and trimers on the surface of the liposomes. In brief, approximately 50% of trimers were lost from the liposomal surface over a period of 7 days when stored at 37° C. (FIG. 30C).

Figure 32A:
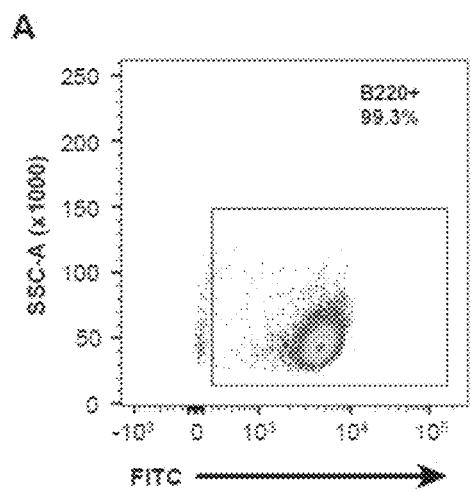
FIGS. 32A-B depict purity of isolated B cells. Splenocytes from b12 knock-in mice were negatively selected for B cells and stained for cell surface markers (A) B220 and (B) CD19.
Figure 32B:
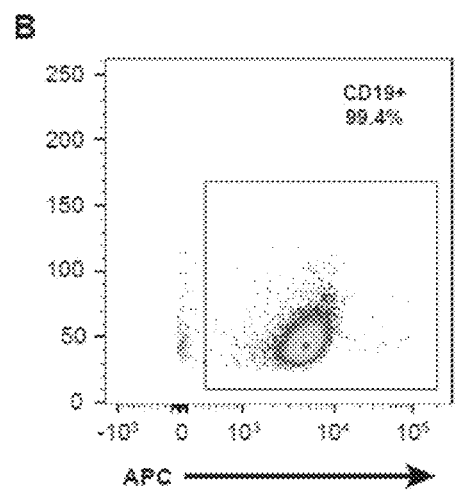

Trimer-conjugated liposomes are more efficient at activating b cells than soluble trimers. Next, Applicants determined if the well-ordered trimers on the liposomes were able to activate B cells following BCR engagement. For this purpose, Applicants used B cells isolated by negative selection from the previously described mature b12-expressing knock-in mice (Ota et al., 2013). The B cells were over 99% pure as characterized by flow cytometry using the B cell markers CD19 and B220 (FIG. 32). The B cells expressing matched b12 H and L chains, possessing either IgM or IgD transmembrane regions, were activated for 18-20 hours with JRFL SOSIP as soluble protein or liposomal preparation and stained with fluorescent antibodies specific for the B cell activation markers CD69, CD86 and MHC class II. The B cell activation markers CD86, CD69, and MHC II were upregulated in a dose-dependent manner in both formulations. However, increases in the levels of CD69 and CD86 were significantly greater following incubation with the trimer-conjugated liposomes compared to the soluble trimers (FIG. 26A), indicating that the multivalent array of HIV-1 trimers was more effective for the induction of BCR signaling and activation. As shown in FIG. 26B, in addition to the increased MFI values associated with liposomal activation, a clear shift in CD69 levels present on the cell-surface was observed in a greater percentage of B cells incubated with the trimer-conjugated liposomes compared to those incubated with soluble trimers. Next, Applicants assessed the expression of proinflammatory cytokines following overnight incubation of the B cells with the two trimer-types. Applicants assessed proinflammatory cytokines since they are often produced at higher quantities benefitting ease of detection and WEHI B cells were shown previously to express TNF-α(Canfield et al., 2005). By ELISA, the levels of TNF-α and IL-6 levels were significantly increased in the culture medium of the B cells incubated with the trimer-conjugated liposomes compared to the soluble trimers (*P=0.0001 and P=0.008 respectively). These data are consistent with the benefit of multivalent trimer particulate array to enhance B cell activation. Applicants performed additional experiments using blank liposomes (4% DGS-NTA(Ni) liposomes lacking trimers) as negative controls compared to the JRFL SOSIP-conjugated liposomes. The induction of cell-surface activation markers and the levels of cytokines induced by the blank liposomes was negligible compared to the trimer-conjugated liposomes, confirming that that the B cells were specifically activated by the trimers arrayed on the surface of the liposomes (FIG. 26D). Since the liposomes used for these experiments were generated without MPLA and R848, Applicants confirmed that their integrity was similar to liposomes formulated with these TLR agonists by negative stain EM (FIG. 30E).

Figure 27A:
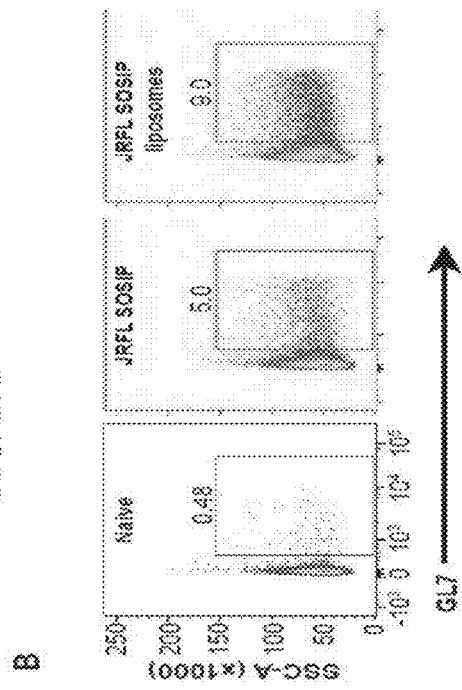
FIGS. 27A-C depict immunization with JRFL SOSIP trimer-conjugated liposomes induced enhanced germinal center (GC) formation. (A) Three groups of five C57Bl/6 mice were subcutaneously administered PBS, soluble JRFL SOSIP trimers or JRFL SOSIP trimer-conjugated liposomes. After 14 days, lymph node B cells were analysed for the activation marker, GL7. The percentage of CD19+ GL7+ cells are enumerated. (B) Representative flow cytometry scatter plots from each group of mice shown in (A) were gated over CD19+ cells from lymph nodes. (C) Two groups of five C57Bl/6 mice were subcutaneously administered either blank liposomes or JRFL SOSIP trimer-conjugated liposomes. After 14 days, the lymph nodes are processed and the percentages of CD19+ GL7+ cells are enumerated. P values were calculated with a two-tailed unpaired t test.
Figure 27B:
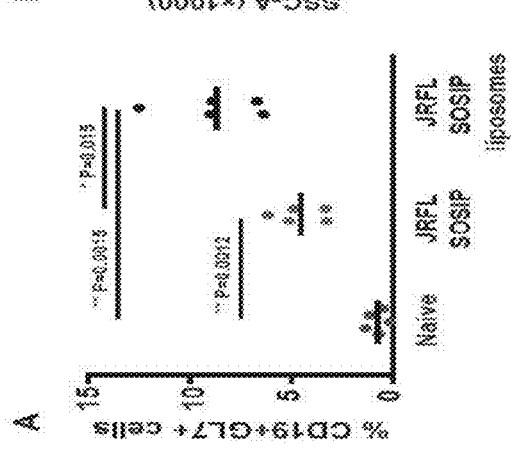
Figure 27C:
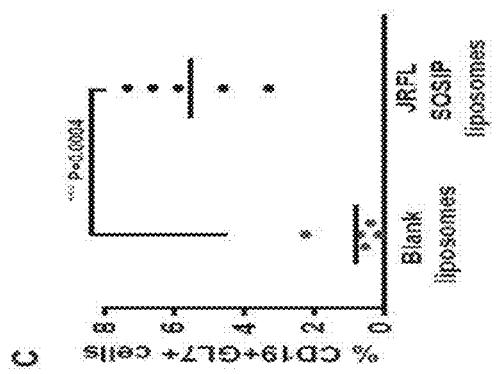

Germinal center (GC) B cells are more efficiently activated by the trimer-conjugated liposomes compared to soluble trimers. GCs are formed in secondary lymphoid organs such as lymph nodes (LNs) and spleen, where activated B cells proliferate and undergo immunoglobulin isotype class switching and somatic hypermutation (Victora and Nussenzweig, 2012). To assess the capacity of the multivalent trimer liposomal array in formation of GCs relative to the soluble trimers, Applicants separated C57BL/6 mice into 3 groups (5 mice per group) and inoculated with PBS (naïve), soluble JRFL SOSIP trimers in ISCOMATRIX™ adjuvant (CSL, Australia), and JRFL SOSIP trimer-containing liposomes in ISCOMATRIX™ adjuvant. Applicants confirmed that the ISCOMATRIX™ adjuvant did not affect the trimers by EM (FIG. 30D). Fourteen days following inoculation, Applicants observed that the draining LNs were larger in the protein/adjuvant-inoculated mice as compared to the naïve mice. Applicants isolated single cells from the LNs of the 5 mice in each of the three groups and performed flow cytometry analysis of CD19+ B cells positive for the GC marker, GL7. The flow cytometry analysis indicated a higher percentage of B cells positive for GL7 in mice inoculated with the JRFL SOSIP-conjugated liposomes compared to mice inoculated with the soluble JRFL SOSIP trimers. Specifically, Applicants observed that the soluble trimers displayed a significantly increased percentage of GL19+GL7+ B cells compared to naïve mice analyzed similarly (P=0.0012) as did the trimer-conjugated liposome mice (P=0.0015). More importantly, the Env trimers arrayed on the surface of the liposomes elicited a statistically significant increase in the percentage of CD19+GL7+ B cells compared to the levels elicited by the soluble trimers (*P=0.0152, FIG. 27A and FIG. 27B), indicating more efficient GC formation was induced by particulate, multivalent trimer array. To ensure that the increase in GL7+ B cells was elicited by the trimers conjugated to liposomal surface and was not due to non-specific activation from the liposomes themselves or inadvertent acquisition of a contaminant during processing (ie, endotoxin), Applicants performed additional control experiments with blank liposomes (4% DGS-NTA(Ni) liposomes lacking trimers) or JRFL SOSIP-conjugated liposomes. Fourteen days post inoculation, the percentage of CD19+ GL7+ cells present in LNs derived from individual mice were analyzed. Mice immunized with the JRFL SOSIP-conjugated liposomes possessed significantly higher GL7+ B cells compared to mice immunized with the blank liposomes (***P=0.0004; FIG. 27C).

Binding and neutralizing antibodies elicited by trimer liposomal array compared to soluble trimers. Given the promising antigenic profile of the well-ordered trimers and the ability of the liposome array of the spike mimetics to activate B cells more efficiently both ex vivo and in vivo compared to the soluble spikes, Applicants next tested the trimer-conjugated liposomes formulated in adjuvant for immunogenicity in a pilot rabbit study. Applicants also sought to determine if inclusion of innate-response-activating TLR agonists into the liposomes would augment antibody responses. Three groups of four rabbits each were immunized with 25 μg of protein either as soluble protein trimer in adjuvant or arrayed on the surface of 4% DGS-NTA(Ni) liposomes containing TLR ligands either with or without adjuvant. Control animals were immunized with blank liposomes containing TLR ligands with adjuvant. Prior to inoculation, the trimer protein concentrations on the liposomes were assessed by protein dye to confirm and quantify the Env content per volume of liposome.

After 3 immunizations, IgG titers were elicited against JRFL SOSIP as measured by ELISA with JRFL SOSIP captured on the plate by the anti-His mAb (see FIG. 28B). The soluble trimers in adjuvant elicited relatively low, but detectable, binding titers to the His-captured SOSIP immunogen. The trimer-conjugated liposomes with the incorporated TLR agonists, but not formulated in the exogenous adjuvant, elicited very little IgG antibody response, indicating that the TLR ligands contributed little to activate the adaptive immune response to Env in vivo. In contrast, the trimer-conjugated liposomes (+TLR ligands) but formulated in exogenous adjuvant, elicited much higher native-trimer binding titers compared to both trimer:liposomes (+TLR ligands) lacking exogenous adjuvant and the soluble trimers formulated in exogenous adjuvant. Taken together, these comparative data sets demonstrated that the liposomal presentation of the trimers rendered them more immunogenic than soluble trimers in the presence of exogenous adjuvant. Blank liposomes in adjuvant, as expected, elicited no detectable trimer binding antibodies in the serum.

Figure 33A:
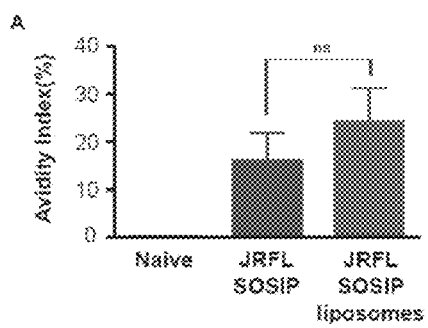
FIGS. 33A-B depict immunogenicity of JRFL SOSIP trimer-conjugated liposomes. (A) Immunizations with JRFL SOSIP:liposomes elicit antibodies with higher avidity than soluble protein. New Zealand white rabbits were immunized 4 times with 25 ug JRFL SOSIP protein as soluble or conjugated to 4% Ni DGPC liposomes. Sera after the 3rd boost was analyzed by ELISA with sodium isothiocyanate (NaSCN) treatment for avidity measurements. Percentage avidity index is defined as (ED50 value with NaSCN treatment/ED50 value without NaSCN treatment)×100. P values were calculated with two-tailed unpaired t test. (B) Mid-point IgG titers of rabbits after 4 and 8 weeks post fourth inoculation analyzed by ELISA with JRFL SOSIP trimers captured on plate via the C-terminal His6tag.
Figure 33B:
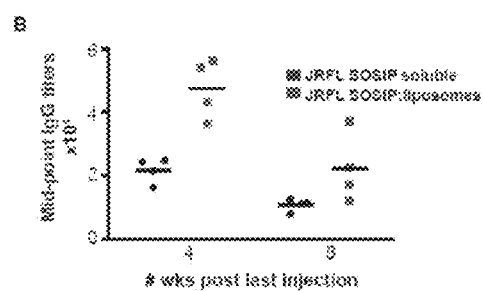

Due to the initial results indicating that the trimer-conjugated liposomes in adjuvant were more immunogenic than the soluble trimers in adjuvant, Applicants performed additional boosts at 5 week intervals and assessed binding titers in a longitudinal manner. Applicants observed that there was a trend for the liposomal trimers to elicit higher binding titers to the native spike mimetics compared to the soluble trimers over the course of immunization (FIG. 28C). Together these data indicated that the trimer-conjugated liposomes were more immunogenic, and that the trimer integrity was maintained in vivo when present on the liposome surface. To further evaluate the quality of the antibody response, Applicants assessed the avidity of the sera to JRFL SOSIP captured on plate by anti-His antibody. The animals immunized with trimer-conjugated liposomes possessed antibodies displaying higher avidity than those receiving soluble trimers, however, the increased avidity was not statistically significant (FIG. 33A).

Next, to determine the quality of the neutralizing response, Applicants performed HIV pseudo-virus neutralization assays (Li et al., 2005). Applicants used sera isolated from individual animals immunized with each trimer-type 14 days following each inoculation with either soluble or trimer-conjugated liposomes. Following both the 3rd and 4th immunization, Applicants detected modest autologous tier 2-like JRFL neutralizing titers from 3 of 4 rabbits receiving the trimer-conjugated liposomes. Only one animal immunized with the soluble trimers displayed weak neutralizing activity at these time points. Although there was a trend for increased neutralization titers elicited by the trimer-conjugated liposomes compared to the soluble trimers, and in more animals per group, as well as boosting of trimer-conjugated liposomes compared to the soluble trimers, these differences were not statistically significant in this small pilot study (FIG. 28D and FIG. 28E).

In this Example, Applicants made use of the new well-ordered Env trimers recently designed in the laboratory to create a high-density multi-variant array of these recombinant glycoprotein HIV spike mimetics on the surface of fully synthetic liposomes. Applicants generated synthetic nickel containing liposomes by incorporating lipids bearing Ni+2 at the polar head group into the lipid bilayer, to capture the C-terminally His6-tagged trimers. Applicants demonstrated by both negative staining and cryo-EM that both the NFL and SOSIP trimers could be arrayed at high-density, were stable, and displayed a favorable antigenic profile following coupling to the surface of the fully synthetic liposomes. Applicants showed that the well-ordered, trimer-conjugated liposomes more efficiently activated B cells ex vivo compared to soluble trimers and better generated GC B cells in vivo in wild-type mice in a statistically significant manner. The trimer-conjugated liposomes displayed a trend to elicit both native binding antibodies and neutralizing antibodies against an HIV-1 tier 2 strain that is more resistant to vaccine-elicited neutralizing antibodies.

These data indicate that Applicants have developed a flexible platform, in which potentially any His-tagged Env trimer can be arrayed at high density. Applicants could array literally hundreds of trimers per particle, perhaps overcoming immune evasion mechanisms that HIV has evolved naturally to reduce activation of host B cells. The non-glycosylated bottom surface of the trimers is blocked by capture using the His tag on the C-terminus of the trimers on the liposomal surface. This non-glycosylated surface was recently shown to be highly immunogenic, potentially diverting neutralizing responses, rendering the SOSIP immunogens incapable of eliciting neutralizing titers in mice (Hu et al., 2015). The high density and uniform array indicates that all three of the His6 tags bound to nickel on the liposome, although Applicants do not have direct evidence for this possibility. Array of the trimers on the liposomes may stabilize more distal regions of Env as the V3 is partially exposed on JRFL Env (more so than most other tier 2 viruses), however, on the JRFL trimer-conjugated liposomes, Applicants could not detect any V3 binding, even with IgG avidity in play. The well-ordered trimers also exhibit enhanced stabilization on the liposomes, as at 4° C. they remain tightly trimeric and arrayed at high density over a period of multiple months.

In terms of B cell activation, the multivalent trimer array on the surface of the liposomes seems to impart advantages in terms of B cell activation both ex vivo and in vivo. Applicants used mouse B cells expressing the bNAb b12, and showed that there is enhanced activation of these B cells, presumably via avidity gained by the high-density multivalent array. Although the increased secretion of IL-6 from the purified B cells following induction by the trimer-conjugated liposomes was consistent with known cytokine profiles, that TNF alpha secretion was also increased was somewhat surprising as this cytokine is not usually secreted by naïve murine B cells, although it has been reported to be secreted by human B cells (Plzakova et al., 2014) and WEHI B cells (Canfield et al., 2005). This may indicate super-antigen effects by trimer multi-valent array or most likely, an altered cytokine profile in these engineered B cells. Less likely, TNF-α secretion is indirect and occurs by dose-dependent activation of a small percentage of myeloid cells in the greater than 99% pure B cell population.

In terms of immunogenicity in vivo, in a pilot rabbit study, the trimer-conjugated liposomes displayed a trend to induce increased binding titers to the native-like trimers compared to the soluble trimers. The enhanced binding titers were detectable beyond a boost or two, an initial indication of longevity of the B cell response. This scenario is reminiscent of the arrayed L1 protein of the highly successful HPV vaccine, which imparts long-lived antibody secreting B cells in humans (Schiller and Chackerian, 2014; Schiller and Lowy, 2015). It will be very interesting to determine if the Env-conjugated liposomes can accomplish prolonged antibody secretion in non-human primates on the pre-clinical pathway toward a vaccine candidate using this type of system. Inclusion of TLR agonists into the liposomal formulation did not render the trimers very immunogenic, indicating that at least for the levels of TLR agonist incorporated here, and the subcutaneous route of administration, these ligands contributed little to the adaptive immune response to the trimers. The data shown here indicates a clear trend of benefit of multivalent array over soluble trimers in vivo in the presence of exogenous adjuvant. However, due to the small numbers of animals per group in this initial study, statistical significance was not achieved. Neutralizing capacity, although not robust in Applicants' study, again displayed a trend to be preferentially induced by the trimer-conjugated liposomes, but again did not achieve statistical significance. Why Applicants do not elicit tier 2 autologous neutralizing responses approaching the levels reported by Sanders et al (Sanders et al., 2015) is unclear, but the JRFL strain used here is generally resistant to vaccine-induced antibodies, as apparently is not the case for BG505 when SOSIPs are inoculated into rabbits. In fact, for BG505, monomeric gp120 can efficiently elicit autologous tier 2 neutralization in rabbits, whereas JRFL gp120 does not elicit autologous tier 2 neutralizing antibodies (Beddows et al., 2007). Further investigation will be needed to determine trimer-virus pairing in regards to the elicitation of autologous tier 2 neutralizing antibodies, as well as the elicitation of neutralizing antibodies in different animal models using matched well-ordered trimer immunogens.

Due to the flexibility of the liposomal system described here, expansion to incorporate well-ordered trimers from other clades onto the liposomal surface is possible either as a diverse array of trimers on independent particles or with different trimers from the same subtype or from different clades arrayed on the same liposome. Such array may have advantages to enhance responses to conserved and common B cell epitopes and neutralizing determinants. Using the approach described here, Applicants demonstrate proof-of-concept using Ni-dependent capture of well-ordered HIV trimers as immunogens. For clinical applications of this approach, Applicants may need to use other divalent cationic lipids possessing cobalt or zinc due to potential nickel inflammatory issues or it might be beneficial to use available maleimide-conjugated lipids to capture trimers possessing a free C-terminal cysteine per protomer of each trimer to reduce any concerns about release from the liposomal surface in vivo.

In summary, Applicants present here initial analysis of multivalent array of ordered HIV trimers conjugated to liposomes in vitro, improved over Applicants' previous Env:proteoliposome studies (Grundner et al., 2002), and their potential advantages as an improved immunogenic platform to more efficiently activate B cell responses ex vivo and in vivo.

Figure 34:
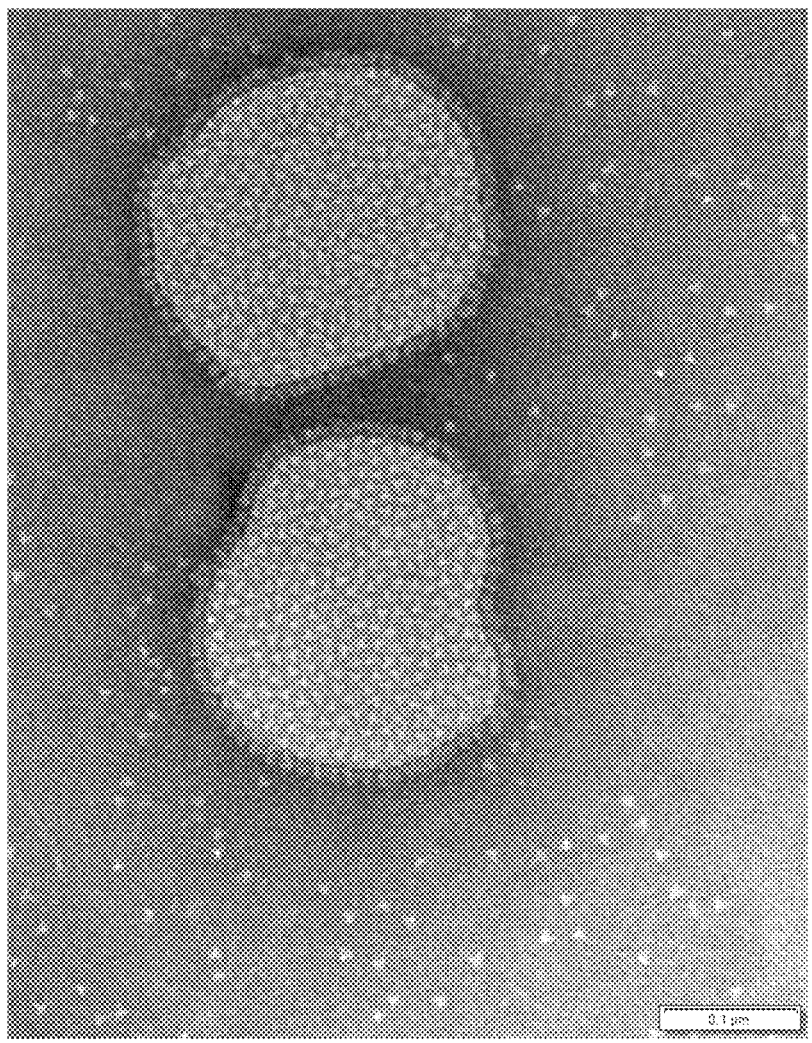
FIG. 34 depicts cobalt Liposomes coupling to BG505 NFL2.
Figure 35:
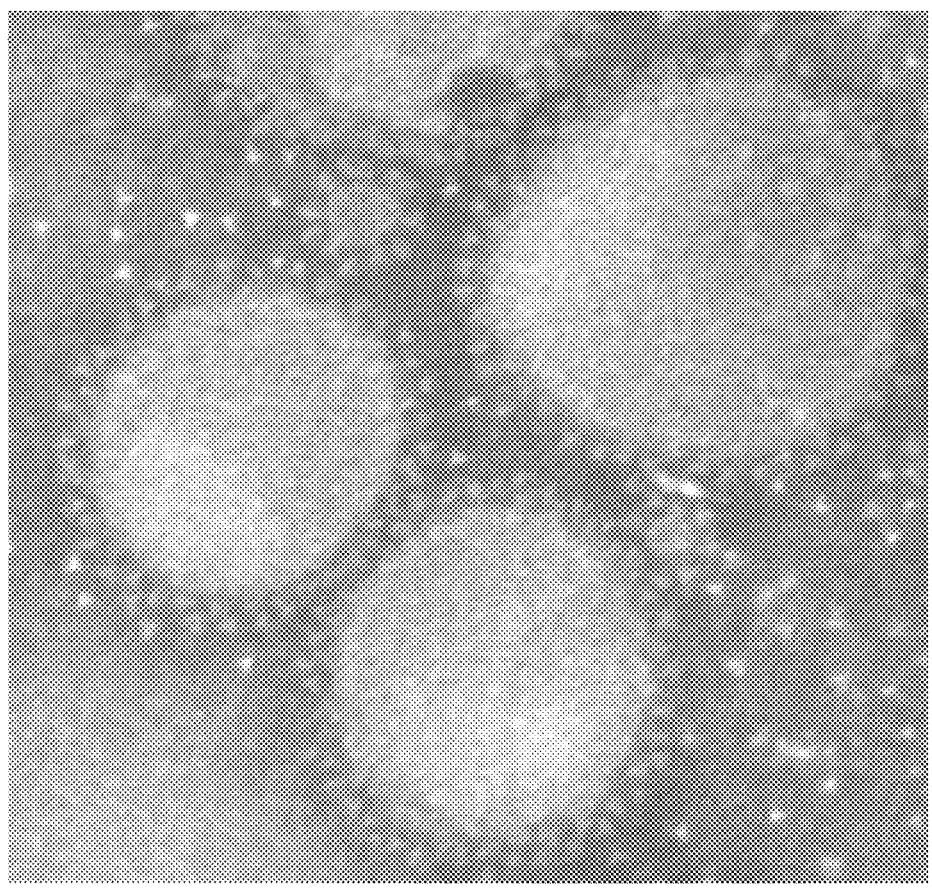
FIG. 35 depicts covalent coupling of Liposomes to free cysteine on BG505 NFL2.

Applicants can now couple liposomes to BG505 Env, and the more stable NFLs versions of 16055, JRFL and BG505 Env. Applicants can successfully couple Env to liposomes incorporating Cobalt as the chelating metal (rather than Nickel). Applicants can covalently couple Env to liposomes by conjugating free cysteine on Env to maleimide group on the liposomes. FIG. 34 depicts cobalt Liposomes coupling to BG505 NFL2 and FIG. 35 depicts covalent coupling of Liposomes to free cysteine on BG505 NFL2.

Expression and purification of recombinant HIV-1 trimer proteins. JRFL SOSIP and JRFL NFL trimers were expressed in serum-free medium by transient transfection of HEK293F cells (Invitrogen) with plasmid DNA as described previously (Sharma et al., 2015). In brief, the secreted proteins were purified by galanthus lectin affinity chromatography followed by size exclusion chromatography (SEC). Next, the trimer peak was subjected to negative selection by the non-neutralizing monoclonal antibody, F105 to retain disordered trimers on the column. The flow through from the F 105 column, containing the well-ordered trimers, was resolved by a second SEC column to isolate a homogenous fraction of well-ordered trimers.

Liposome preparation, protein conjugation and lipid and protein quantitation. For DLS, Octet, EM, GC analysis, and immunization, the liposomes were composed of a molar ratio of 50:36:4:5:5 of DGPC, cholesterol, DGS-NTA(Ni), Monophosphoryl lipid A (MPLA) (synthetic) PHAD™ (Avanti Polar Lipids), and R848 (InvivoGen). For ex-vivo studies, liposomes were composed of a molar ratio of 60:36:4 of 1,2-distearoyl-sn-glycero-3-phosphocholine (DGPC) (Avanti Polar Lipids), cholesterol (Sigma Life-science), and [(5-amino-1-carboxypentyl) imino di acetic acid) succinyl] (nickel salt) (DGS-NTA(Ni)) (Avanti Polar Lipids). To form the liposomes, the above constituents were mixed in the appropriate ratios in chloroform, incubated over glass and chloroform was evaporated in the presence of gaseous nitrogen. The resulting lipid film was dried further O/N in a desiccator. The lipids were hydrated in PBS for 2 hours at 37° C. with constant shaking followed by vigorous sonication for 30 seconds. Next, the liposomes were extruded for a minimum of 15 times through 1 µm, 0.8 µm, 0.4 µm, 0.2 µm, and 0.1 µm filters using a hand-held mini-extrusion device (Avanti Polar Lipids) at room temperature (RT). For conjugation of protein to the liposomes, 2.2 mg of trimer protein was added to 500 µl of liposomes and incubated at RT for 2 hours. The unbound protein was removed from the liposomes by passing the liposome mixture through Superdex 100 column. The liposome fractions were collected, pooled and stored at 4° C.

JRFL SOSIP and JRFL NFL trimers conjugated on the liposomes were quantitated using a standard curve generated by either soluble JRFL SOSIP or JRFL NFL trimers, respectively, using Advanced Protein Assay Reagent (Cytoskeleon) according to manufacturer's instructions. Phosphorous in liposomes was estimated by a colorimetric assay reported earlier. Briefly, phosphorous (Sigma) standard curve was generated and used to determine the amounts of phosphorous in the liposome samples. First, the organic samples were digested to inorganic phosphate by heating the samples at 215° C. for 25 min, followed by addition of hydrogen peroxide and continued heating for additional 30 min. Next, ammonium molybdate and ascorbic acid were added sequentially and again the samples were heated at 100° C. for 7 min. The absorbance at 820 nm was determined for both the standard and the experimental samples.

Electron microscopy. For negative stain EM, liposomes were applied for 3 minutes onto a glow discharged carbon-coated 400-Cu mesh grids (Electron Microscopy Sciences, Hatfield, Pa.). Excess sample was removed and the grids were immediately placed on a droplet of 2% phosphotungstic acid solution (pH 6.9) for 2 minutes. Excess stain was removed and the grids were allowed to dry thoroughly. Grids were examined on a Philips CM100 electron microscope (FEI, Hillsbrough Oreg.) at 80 kV, and images were acquired with a Megaview III charge-coupled device (CCD) camera (Olympus Soft Imaging Solutions Germany). For cryo EM, samples were preserved undiluted in vitrified ice supported by holey carbon films on 400-mesh copper grids. Samples were prepared by applying 3 µl drop of sample suspension to a clean grid blotting away excess with filter paper and immediately proceeded with vitrification in liquid ethane. Grids were stored under liquid nitrogen until transferred to the electron microscope for imaging. Electron microscopy was performed using an FEI Tecnai T12 electron microscope operating at 120 keV equipped with an FEI Eagle 4k×4k CCD camera. Vitreous ice grids were transferred into the electron microscope using a cryostage that maintains the grids at a temperature below −170° C.

Bio-layer light interferometry (BLI). Binding interactions between monoclonal antibodies (mAbs) and the trimers conjugated to the liposome surface or soluble trimers were examined by BLI using an Octet RED system (ForteBio). Biotinylated Wheat Germ Agglutinin (WGA) (Vector Laboratories) was captured on Streptavidin biosensors (ForteBio) at 50 µg/ml in PBS-B (PBS with 0.1% BSA) for 180 sec followed by wash for 180 sec in PBS-B. Next, the liposomes conjugated with trimers (10 µg/ml) were loaded onto the WGA sensors for 30 min followed by wash for 60 min. The biosensors were immersed in PBS-B aliquoted in 96 well plates to generate a baseline. Next, the biosensors were immersed in a separate 96 well plate filled with PBS-B containing the mAbs (20 µg/ml) for 5 min to allow association of the immobilized trimers with antibody. Association was followed by dissociation in PBS-B for 30 min. A constant temperature of 30° C. was maintained inside the instrument during all reactions. A reference sensor was generated during each experimental run to ensure that there was minimal level of non-specific binding of mAbs to the WGA sensors.

B-Cell activation assay. B-cells from spleen and lymph nodes were purified by negative selection using MACS® separation (Miltenyi Biotec) that uses monoclonal antibodies specific for T cells and monocytes conjugated to the paramagnetic bead to retain all cells but B cells on the solid phase. Cells were plated as 1×105 cells/well in a 96 well plate and stimulated with 50 µg/ml, 5 µg/ml and 0.5 µg/ml of soluble JRFL SOSIP trimers, JRFL SOSIP trimers conjugated to the 4% DGS-NTA(Ni) liposomes or 4% DGS-NTA(Ni) liposomes for 18-20 hours. The supernatants were stored at −20° C. for TNF-α and IL-6 ELISAs. Next, the cells were stained with fluorescent antibodies specific for CD86, CD69, and MEW II prior to analysis by Flow Cytometry. The experiment was performed in two independent experiments from different mature b12 mAb transgenic mice (Ota et al., 2013).

Animal inoculations. New Zealand white female rabbits were inoculated subcutaneously with 25 µg of protein as either soluble or conjugated to 4% DGS-NTA(Ni) liposomes and formulated in 20% of Adjuplex™ (Advanced BioAdjuvants) in a total volume of 150 µl. For the control group, blank 4% DGS-NTA(Ni) liposomes with MPLA and R848 were formulated in 20% of Adjuplex™. The liposomes contained 30 µg MPLA and 6.5 µg R848 per each injection. Test bleeds were collected two weeks after each inoculation. To determine in vivo GC formation, 3 groups of 6 weeks old C57BL/6 mice (5 mice per group) were subcutaneously inoculated in the hind legs by hock injection (Kamala, 2007) with either PBS, 10 µg of soluble JRFL SOSIP trimeric protein formulated in 1 unit of ISCOMATRIX, 10 µg of JRFL SOSIP trimeric protein conjugated to 4% DGS-NTA (Ni) liposomes formulated in 1 unit of ISCOMATRIX, or 4% DGS-NTA(Ni) liposomes formulated in 1 unit of ISCOMATRIX in a total volume of 100 µl. Fourteen days following inoculation, the draining popliteal lymph nodes were isolated and prepared as single cell suspensions and subjected to staining with mAbs as described below.

ELISA. ELISAs were performed in 96-well MaxiSorp plates (Nalgene Nunc International). Plates were coated for 4 hrs at RT with anti-His tag mAb (2 µg/ml; R&D Systems). After blocking the plates with non-fat milk and fetal bovine serum (FBS) for overnight at 4° C., the plates were incubated with JRFL SOSIP trimeric protein at 2 µg/ml for 2 hr at room temperature. Next, the plates were incubated with five-fold serial dilutions of the immune sera starting at 1:200, and after 1 hr were washed with buffer, followed by incubation with HRP-conjugated anti-rabbit IgG (1:5000) or HRP-conjugated anti-rabbit IgM (1:5000) for detection. The plates were developed by a chromogenic substrate for HRP, 3,3', 5, 5'-tetramethylbenzidine (Life Technologies). Reactions were stopped by the addition of sulfuric acid and absorbance was measured at 450 nm. For ex-vivo studies, culture supernatants were collected and cytokine ELISAs were performed using DuoSet ELISA Development Kits (R&D Systems) according to manufacturer's instructions.

Neutralization assay. The pseudoviruses were prepared and neutralization assays were performed as described previously (Li et al., 2005). Briefly, rabbit sera were diluted and pre-incubated with virus (200,000 RLU) for 30 min at 37 C before adding to 10,000 TZM-bl reporter cells per well. These cells contain an integrated luciferase gene under the control of the Tat-sensitive HIV LTR. Virus was incubated for cells the cells for 48 hrs to allow infection and potential luciferase induction, after which the cells were lysed, and relative luciferase units were measured by a Victor luminometer (PerkinElmer).

Flow cytometry of mouse LN-derived b cells. Murine lymph nodes were gently disrupted through a 70 µm cell sieve, followed by extensive washing. All cells were labeled with live/dead cell viability reagent (Invitrogen) followed by blocking with anti-mouse CD16/CD32 (BD Pharmingen). Next, the cells were incubated with APC anti-mouse CD19 and FITC anti-mouse GL7 (BioLegend) and post-fixed with paraformaldehyde before acquiring cells on an LSRII (Becton Dickinson) to determine fluorescent mAb binding. Data were analysed with FlowJo software (TreeStar).

Binding analysis of selected mAbs to JRFL SOSIP. Binding interactions between selected trimer-preferring and CDbs-directed antibodies to JRFL SOSIP trimers were examined by biolayer light interferometry (BLI) using Octet Red system (ForteBio). The mAbs were captured on the surface of the anti-human Fc sensors from a solution of 5 µg/ml in PBS for 60s at 1,000 rpm. Bio-sensors were then immersed in a solution of the JRFL SOSIP trimers (diluted to 200 nM) for 600s at 1,000 rpm to allow association of the immobilized antibodies with the analyte. Association was followed by dissociation in PBS for 600s at 1,000 rpm.

Electron microscopy. JRFL SOSIP-conjugated liposomes were mixed at a 10% (v/v) with ISCOMATRIX and Adjuplex and incubated at 37° C. for 1 h. 5 µl of the mixture was stained with phosphor tungstate on carbon-coated Cu grids. The grids were examined on a Philips CM100 electron microscope. (FEI, Hillsbrough Oreg.) at 80 kV and images were acquired with a Megaview III charge-coupled device (CCD) camera.

Avidity measurements. For avidity measurements, the ELISAs were developed as described previously, with an additional washing step. After the incubation of the sera, the plates were washed and incubated for 15 min with 1.5M sodium isothio cynate (NaSCN) in PBS, while duplicate plates were incubated with an equal volume of PBS. The plates were then washed again to remove dissociated antibody and detection of bound antibody was performed.

REFERENCES

Arsov, Z., and Quaroni, L. (2007). Direct interaction between cholesterol and phosphatidylcholines in hydrated membranes revealed by ATR-FTIR spectroscopy. Chem Phys Lipids 150, 35-48.

Beddows, S., Franti, M., Dey, A. K., Kirschner, M., Iyer, S. P., Fisch, D. C., Ketas, T., Yuste, E., Desrosiers, R. C., Klasse, P. J., et al. (2007). A comparative immunogenicity study in rabbits of disulfide-stabilized, proteolytically cleaved, soluble trimeric human immunodeficiency virus type 1 gp140, trimeric cleavage-defective gp140 and monomeric gp120. Virology 360, 329-340.

Burton, D. R., Desrosiers, R. C., Doms, R. W., Koff, W. C., Kwong, P. D., Moore, J. P., Nabel, G. J., Sodroski, J., Wilson, I. A., and Wyatt, R. T. (2004). HIV vaccine design and the neutralizing antibody problem. Nature Immunology 5, 233-236.

Burton, D. R., Pyati, J., Koduri, R., Sharp, S. J., Thornton, G. B., Parren, P. W., Sawyer, L. S., Hendry, R. M., Dunlop, N., Nara, P. L., and et al. (1994). Efficient neutralization of primary isolates of HIV-1 by a recombinant human monoclonal antibody. Science 266, 1024-1027.

Caldeira Jdo, C., Medford, A., Kines, R. C., Lino, C. A., Schiller, J. T., Chackerian, B., and Peabody, D. S. (2010). Immunogenic display of diverse peptides, including a broadly cross-type neutralizing human papillomavirus L2 epitope, on virus-like particles of the RNA bacteriophage PP7. Vaccine 28, 4384-4393.

Canfield, S., Lee, Y., Schroder, A., and Rothman, P. (2005). Cutting edge: IL-4 induces suppressor of cytokine signaling-3 expression in B cells by a mechanism dependent on activation of p38 MAPK. J Immunol 174, 2494-2498.

Deml, L., Kratochwil, G., Osterrieder, N., Knuchel, R., Wolf, H., and Wagner, R. (1997). Increased incorporation of chimeric human immunodeficiency virus type 1 gp120 proteins into Pr55gag virus-like particles by an Epstein-Barr virus gp220/350-derived transmembrane domain. Virology 235, 10-25.

Falkowska, E., Le, K. M., Ramos, A., Doores, K. J., Lee, J. H., Blattner, C., Ramirez, A., Derking, R., van Gils, M. J., Liang, C. H., et al. (2014). Broadly neutralizing HIV antibodies define a glycan-dependent epitope on the prefusion conformation of gp41 on cleaved envelope trimers. Immunity 40, 657-668.

Grundner, C., Mirzabekov, T., Sodroski, J., and Wyatt, R. (2002). Solid-phase proteoliposomes containing human immunodeficiency virus envelope glycoproteins. Journal of virology 76, 3511-3521.

Guenaga, J., de Val, N., Tran, K., Feng, Y., Satchwell, K., Ward, A. B., and Wyatt, R. T. (2015). Well-ordered trimeric HIV-1 subtype B and C soluble spike mimetics generated by negative selection display native-like properties. PLoS Pathog 11, e1004570.

Hu, J. K., Crampton, J. C., Cupo, A., Ketas, T., van Gils, M. J., Sliepen, K., de Taeye, S. W., Sok, D., Ozorowski, G., Deresa, I., et al. (2015). Murine antibody responses to cleaved soluble HIV-1 envelope trimers are highly restricted in specificity. Journal of virology.

Julien, J. P., Cupo, A., Sok, D., Stanfield, R. L., Lyumkis, D., Deller, M. C., Klasse, P. J., Burton, D. R., Sanders, R. W., Moore, J. P., et al. (2013). Crystal structure of a soluble cleaved HIV-1 envelope trimer. Science 342, 1477-1483.

Kamala, T. (2007). Hock immunization: a humane alternative to mouse footpad injections. J Immunol Methods 328, 204-214.

Kovacs, J. M., Noeldeke, E., Ha, H. J., Peng, H., Rits-Volloch, S., Harrison, S. C., and Chen, B. (2014). Stable, uncleaved HIV-1 envelope glycoprotein gp140 forms a tightly folded trimer with a native-like structure. Proceedings of the National Academy of Sciences of the United States of America 111, 18542-18547.

Li, M., Gao, F., Mascola, J. R., Stamatatos, L., Polonis, V. R., Koutsoukos, M., Voss, G., Goepfert, P., Gilbert, P., Greene, K. M., et al. (2005). Human immunodeficiency virus type 1 env clones from acute and early subtype B infections for standardized assessments of vaccine-elicited neutralizing antibodies. Journal of virology 79, 10108-10125.

Li, Y., O'Dell, S., Wilson, R., Wu, X., Schmidt, S. D., Hogerkorp, C. M., Louder, M. K., Longo, N. S., Poulsen, C., Guenaga, J., et al. (2012). HIV-1 neutralizing antibodies display dual recognition of the primary and coreceptor binding sites and preferential binding to fully cleaved envelope glycoproteins. Journal of virology 86, 11231-11241.

Liao, H. X., Lynch, R., Zhou, T., Gao, F., Alam, S. M., Boyd, S. D., Fire, A. Z., Roskin, K. M., Schramm, C. A., Zhang, Z., et al. (2013). Co-evolution of a broadly neutralizing HIV-1 antibody and founder virus. Nature 496, 469-476.

McLellan, J. S., Pancera, M., Carrico, C., Gorman, J., Julien, J. P., Khayat, R., Louder, R., Pejchal, R., Sastry, M., Dai, K., et al. (2011). Structure of HIV-1 gp120 V1/V2 domain with broadly neutralizing antibody PG9. Nature 480, 336-343.

Ota, T., Doyle-Cooper, C., Cooper, A. B., Doores, K. J., Aoki-Ota, M., Le, K., Schief, W. R., Wyatt, R. T., Burton, D. R., and Nemazee, D. (2013). B cells from knock-in mice expressing broadly neutralizing HIV antibody b12 carry an innocuous B cell receptor responsive to HIV vaccine candidates. J Immunol 191, 3179-3185.

Pancera, M., Zhou, T., Druz, A., Georgiev, I. S., Soto, C., Gorman, J., Huang, J., Acharya, P., Chuang, G. Y., Ofek, G., et al. (2014). Structure and immune recognition of trimeric pre-fusion HIV-1 Env. Nature 514, 455-461.

Pejawar-Gaddy, S., Kovacs, J. M., Barouch, D. H., Chen, B., and Irvine, D. J. (2014). Design of lipid nanocapsule delivery vehicles for multivalent display of recombinant Env trimers in HIV vaccination. Bioconjug Chem 25, 1470-1478.

Pejchal, R., Walker, L. M., Stanfield, R. L., Phogat, S. K., Koff, W. C., Poignard, P., Burton, D. R., and Wilson, I. A. (2010). Structure and function of broadly reactive antibody PG16 reveal an H3 subdomain that mediates potent neutralization of HIV-1. Proceedings of the National Academy of Sciences of the United States of America 107, 11483-11488.

Plzakova, L., Kubelkova, K., Krocova, Z., Zarybnicka, L., Sinkorova, Z., and Macela, A. (2014). B cell subsets are activated and produce cytokines during early phases of *Francisella tularensis* LVS infection. Microb Pathog 75, 49-58.

Posner, M. R., Cavacini, L. A., Emes, C. L., Power, J., and Byrn, R. (1993). Neutralization of HIV-1 by F105, a human monoclonal antibody to the CD4 binding site of gp120. J Acquir Immune Defic Syndr 6, 7-14.

Ringe, R. P., Yasmeen, A., Ozorowski, G., Go, E. P., Pritchard, L. K., Guttman, M., Ketas, T. A., Cottrell, C. A., Wilson, I. A., Sanders, R. W., et al. (2015). Influences on the Design and Purification of Soluble, Recombinant Native-Like HIV-1 Envelope Glycoprotein Trimers. Journal of virology 89, 12189-12210.

Safaeian, M., Porras, C., Pan, Y., Kreimer, A., Schiller, J. T., Gonzalez, P., Lowy, D. R., Wacholder, S., Schiffman, M., Rodriguez, A. C., et al. (2013). Durable antibody responses following one dose of the bivalent human papillomavirus L 1 virus-like particle vaccine in the Costa Rica Vaccine Trial. Cancer Prev Res (Phila) 6, 1242-1250.

Sanders, R. W., Derking, R., Cupo, A., Julien, J. P., Yasmeen, A., de Val, N., Kim, H. J., Blattner, C., de la Pena, A. T., Korzun, J., et al. (2013). A next-generation cleaved, soluble HIV-1 Env trimer, BG505 SOSIP.664 gp140, expresses multiple epitopes for broadly neutralizing but not non-neutralizing antibodies. PLoS Pathog 9, e1003618.

Sanders, R. W., van Gils, M. J., Derking, R., Sok, D., Ketas, T. J., Burger, J. A., Ozorowski, G., Cupo, A., Simonich, C., Goo, L., et al. (2015). HIV-1 VACCINES. HIV-1 neutralizing antibodies induced by native-like envelope trimers. Science 349, aac4223.

Schiller, J., and Chackerian, B. (2014). Why HIV virions have low numbers of envelope spikes: implications for vaccine development. PLoS Pathog 10, e1004254.

Schiller, J. T., and Lowy, D. R. (2015). Raising expectations for subunit vaccine. J Infect Dis 211, 1373-1375.

Sharma, S. K., de Val, N., Bale, S., Guenaga, J., Tran, K., Feng, Y., Dubrovskaya, V., Ward, A. B., and Wyatt, R. T. (2015). Cleavage-independent HIV-1 Env trimers engineered as soluble native spike mimetics for vaccine design. Cell Rep 11, 539-550.

Sok, D., van Gils, M. J., Pauthner, M., Julien, J. P., Saye-Francisco, K. L., Hsueh, J., Briney, B., Lee, J. H., Le, K. M., Lee, P. S., et al. (2014). Recombinant HIV envelope trimer selects for quaternary-dependent antibodies targeting the trimer apex. Proceedings of the National Academy of Sciences of the United States of America 111, 17624-17629.

Stanfield, R. L., Gorny, M. K., Williams, C., Zolla-Pazner, S., and Wilson, I. A. (2004). Structural rationale for the broad neutralization of HIV-1 by human monoclonal antibody 447-52D. Structure 12, 193-204.

Tran, E. E., Borgnia, M. J., Kuybeda, O., Schauder, D. M., Bartesaghi, A., Frank, G. A., Sapiro, G., Milne, J. L., and Subramaniam, S. (2012). Structural mechanism of trimeric HIV-1 envelope glycoprotein activation. PLoS Pathog 8, e1002797.

Tran, K., Poulsen, C., Guenaga, J., de Val, N., Wilson, R., Sundling, C., Li, Y., Stanfield, R. L., Wilson, I. A., Ward, A. B., et al. (2014). Vaccine-elicited primate antibodies use a distinct approach to the HIV-1 primary receptor binding site informing vaccine redesign. Proceedings of the National Academy of Sciences of the United States of America 111, E738-747.

Trkola, A., Purtscher, M., Muster, T., Ballaun, C., Buchacher, A., Sullivan, N., Srinivasan, K., Sodroski, J., Moore, J. P., and Katinger, H. (1996). Human monoclonal antibody 2G12 defines a distinctive neutralization epitope on the gp120 glycoprotein of human immunodeficiency virus type 1. Journal of virology 70, 1100-1108.

Victora, G. D., and Nussenzweig, M. C. (2012). Germinal centers. Annu Rev Immunol 30, 429-457.

Wu, X., Zhou, T., Zhu, J., Zhang, B., Georgiev, I., Wang, C., Chen, X., Longo, N. S., Louder, M., McKee, K., et al. (2011). Focused evolution of HIV-1 neutralizing antibodies revealed by structures and deep sequencing. Science 333, 1593-1602.

The invention is further described by the following numbered paragraphs:

1. An engineered or non-naturally occurring Clade A BG505-NFL2 Env trimer comprising one or more proline mutations, wherein the mutation is S553P, N554P, E560P, Q562P, Q563P, and/or any combination thereof.

2. An engineered or non-naturally occurring Clade C 16055-NFL2 Env trimer comprising one or more proline mutations, wherein the mutation is L555P, Q652P, Q653P, L565P, L566P, and/or any combination thereof.

3. An engineered or non-naturally occurring Clade B JRFL-NFL2 Env trimer comprising one or more proline mutations, wherein the mutation is L555P, N554P, I559P, Q562P, Q563P, S649D or any combination thereof.

4. A method of eliciting an immune response in a mammal comprising administering the trimer of any one of paragraphs 1-3.

5. The method of paragraph 4, wherein the trimer is administered with an adjuvant.

6. The method of paragraph 5, wherein the adjuvant comprises a lecithin, preferably, wherein the adjuvant is a lecithin is combined with an acrylic polymer, a lecithin coated oil droplet in an oil-in-water emulsion or a lecithin and an acrylic polymer in an oil-in-water emulsion.

7. The method of paragraph 5, wherein the adjuvant is ISCOMATRIX or Adjuplex.

8. The method of paragraph 5, wherein the adjuvant comprises alum.

9. The method of paragraph 4, wherein the trimer is administered in a liposome or in a nanoparticle.

10. The method of paragraph 4, wherein the trimer is fixed, preferably wherein the trimer is fixed in glutaraldehyde.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An engineered or non-naturally occurring Clade A BG505-NFL2 Env trimer comprising one or more proline mutations, wherein the mutation is S553P, N554P, E560P, Q562P, Q563P, or any combination thereof.

2. An engineered or non-naturally occurring Clade C 16055-NFL2 Env trimer comprising one or more proline mutations, wherein the mutation is L555P, Q652P, Q653P, L565P, L566P, or any combination thereof.

3. An engineered or non-naturally occurring Clade B JRFL-NFL2 Env trimer comprising one or more proline mutations, wherein the mutation is L555P, N554P, I559P, Q562P, Q563P, S649D or any combination thereof.

4. A composition comprising the trimer of claim 1 conjugated to a liposome.

5. A composition comprising the trimer of claim 2 conjugated to a liposome.

6. A composition comprising the trimer of claim 3 conjugated to a liposome.

7. A method of eliciting an immune response in a mammal comprising administering the trimer of claim 1.

8. A method of eliciting an immune response in a mammal comprising administering the trimer of claim 2.

9. A method of eliciting an immune response in a mammal comprising administering the trimer of claim 3.

10. The composition of claim 4, wherein the trimer is fixed.

11. The composition of claim 5, wherein the trimer is fixed.

12. The composition of claim 6, wherein the trimer is fixed.

13. The composition of claim 10, wherein the trimer is fixed in glutaraldehyde.

14. The composition of claim 11, wherein the trimer is fixed in glutaraldehyde.

15. The composition of claim 12, wherein the trimer is fixed in glutaraldehyde.

16. A method of eliciting an immune response in a mammal comprising administering the composition of claim 4.

17. A method of eliciting an immune response in a mammal comprising administering the composition of claim 5.

18. A method of eliciting an immune response in a mammal comprising administering the composition of claim 6.

* * * * *